(12) United States Patent
Sato et al.

(10) Patent No.: US 6,602,471 B1
(45) Date of Patent: Aug. 5, 2003

(54) ADSORPTION AMOUNT SENSOR AND COKING SENSOR FOR INTERNAL COMBUSTION ENGINE

(75) Inventors: Masahiro Sato, Saitama-ken (JP); Yoshihisa Iwaki, Saitama-ken (JP); Yuji Yasui, Saitama-ken (JP); Takashi Haga, Saitama-ken (JP); Masaki Ueno, Saitama-ken (JP); Tetsuo Endo, Saitama-ken (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/568,125

(22) Filed: May 10, 2000

(30) Foreign Application Priority Data

| May 14, 1999 | (JP) | ............................................. 11-133619 |
| May 14, 1999 | (JP) | ............................................. 11-133620 |
| Jan. 31, 2000 | (JP) | ........................................ 2000-023085 |

(51) Int. Cl.$^7$ .......................... G01N 30/96; G01N 7/00; G01N 33/00

(52) U.S. Cl. .......................... 422/88; 422/68.1; 422/83; 73/23.31; 436/139

(58) Field of Search .............................. 422/88, 90, 98; 73/23.31; 204/424; 29/25.42; 60/297, 274; 436/139

(56) References Cited

U.S. PATENT DOCUMENTS

| 5,143,696 A | * | 9/1992 | Haas et al. .................... 422/90 |
| 5,296,196 A | * | 3/1994 | Takeshima .................... 422/98 |
| 5,419,124 A | * | 5/1995 | Adamczyk, Jr. et al. ...... 60/274 |
| 5,787,707 A | * | 8/1998 | Hertl et al. .................... 60/297 |
| 5,857,250 A | * | 1/1999 | Riley et al. ................. 29/25.42 |
| 5,948,966 A | * | 9/1999 | Takahashi et al. .......... 73/23.31 |
| 5,965,451 A | * | 10/1999 | Plog et al. .................... 436/139 |
| 6,254,749 B1 | * | 7/2001 | Yokota et al. ............... 204/424 |

* cited by examiner

Primary Examiner—Jill Warden
Assistant Examiner—Brian Sines
(74) Attorney, Agent, or Firm—Arent Fox Kinter Plotkin & Kahn

(57) ABSTRACT

There are provided an adsorption amount sensor which is capable of accurately detecting an amount of hydrocarbons or water adsorbed by a zeolite of a hydrocarbon adsorber, even during operation of an engine, as well as a coking sensor which is capable of accurately detecting an amount of coke deposition on inner surfaces of a pipe of an internal combustion engine, even during operation of an engine. The adsorption amount sensor has a plurality of electrodes arranged in the vicinity of the hydrocarbon adsorber in a manner opposed to each other and each carrying a zeolite thereon. The amount of hydrocarbons adsorbed is detected by using a parameter indicative of changes in at least one of a resistance value between the electrodes and an electrical capacitance between the electrodes. The coking sensor has a plurality of electrodes arranged within the pipe of the engine in a manner opposed to each other and each having a surface thereof coated with an insulating material. The amount of coke deposition is detected by using a parameter indicative of changes in at least one of a resistance value between the electrodes and an electrical capacitance between the electrodes.

19 Claims, 21 Drawing Sheets

F I G. 1
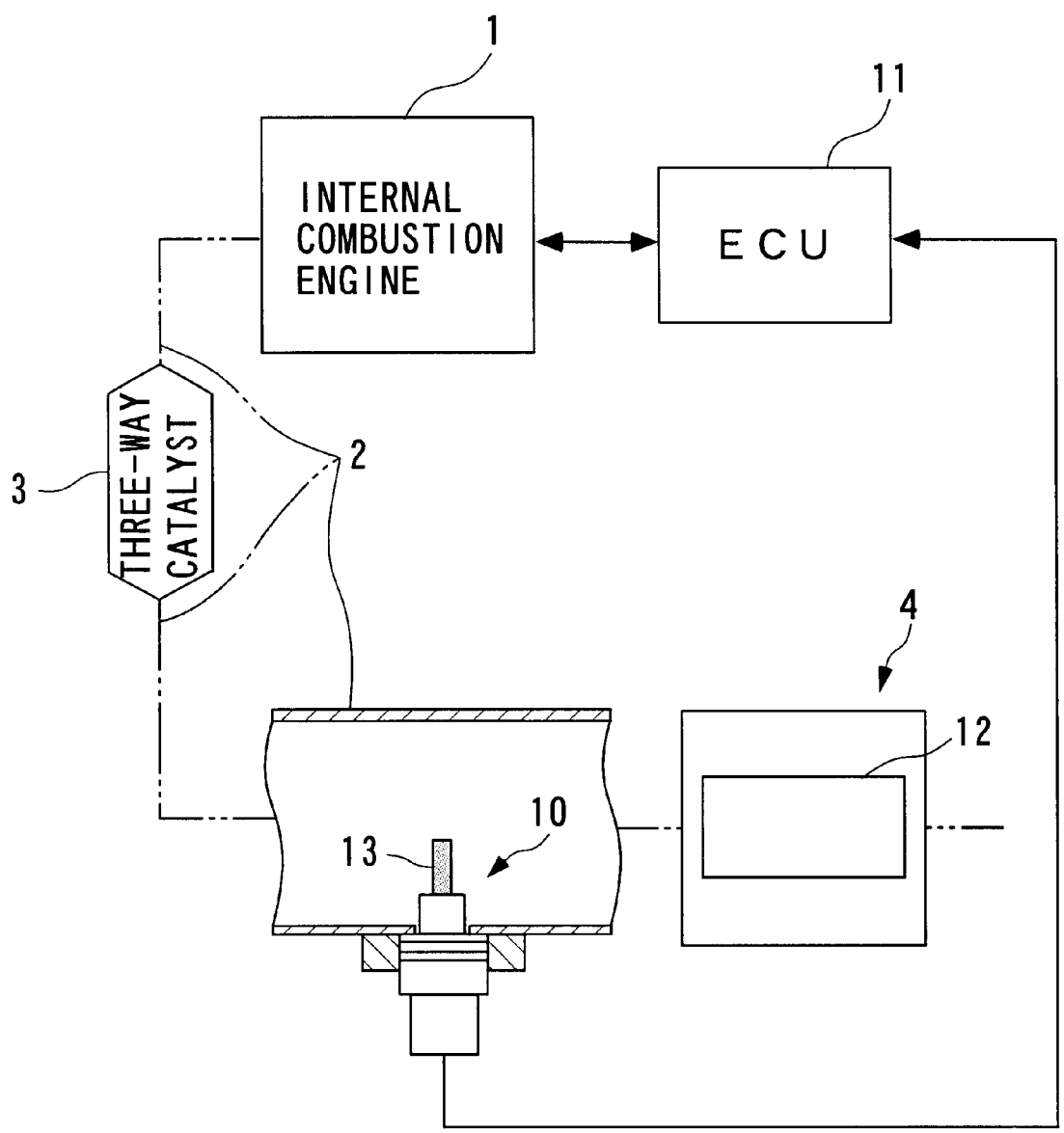

F I G. 4
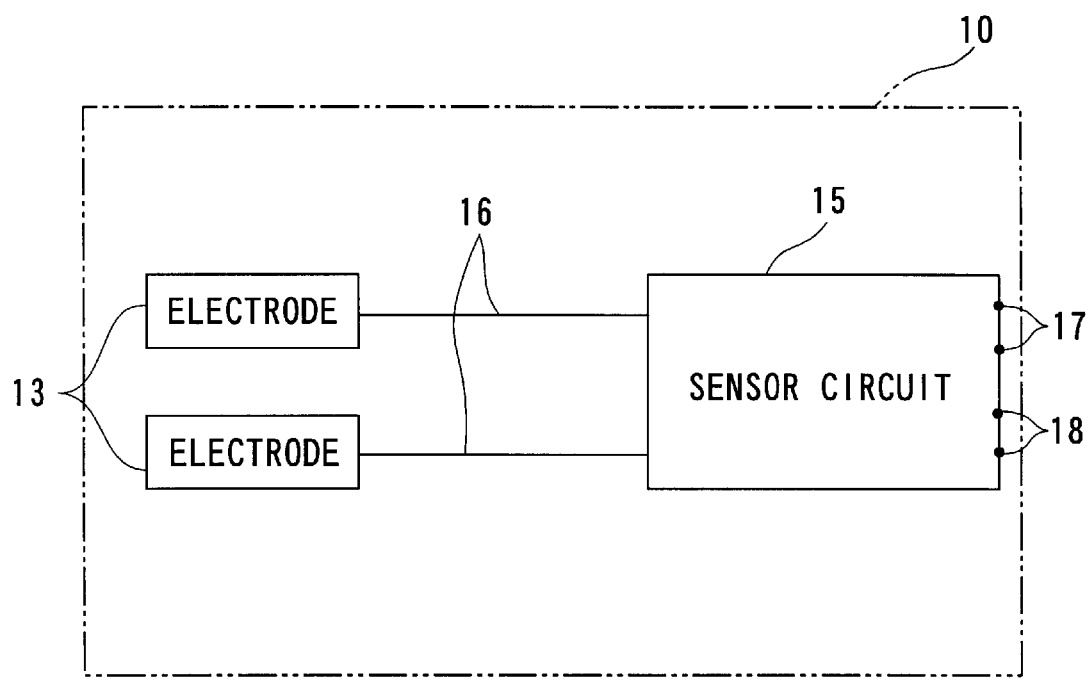

F I G. 8A
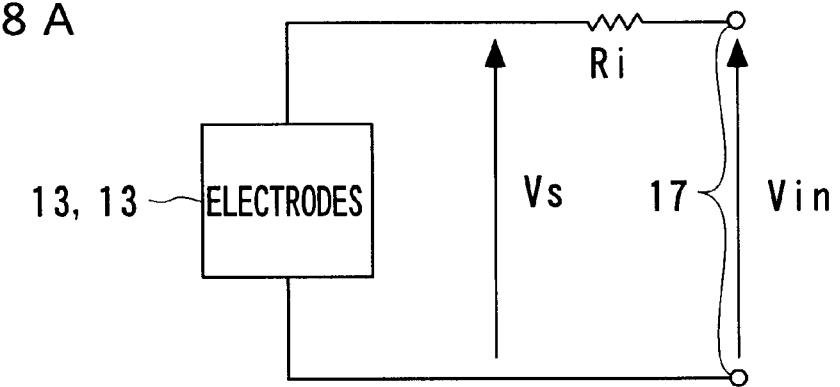
F I G. 8B
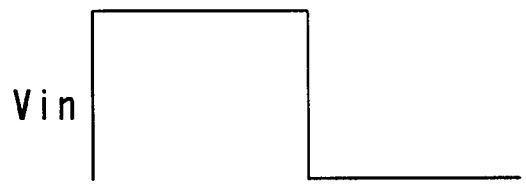
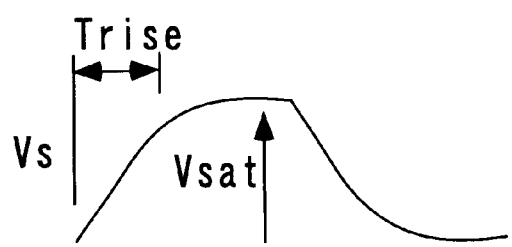

F I G. 1 8
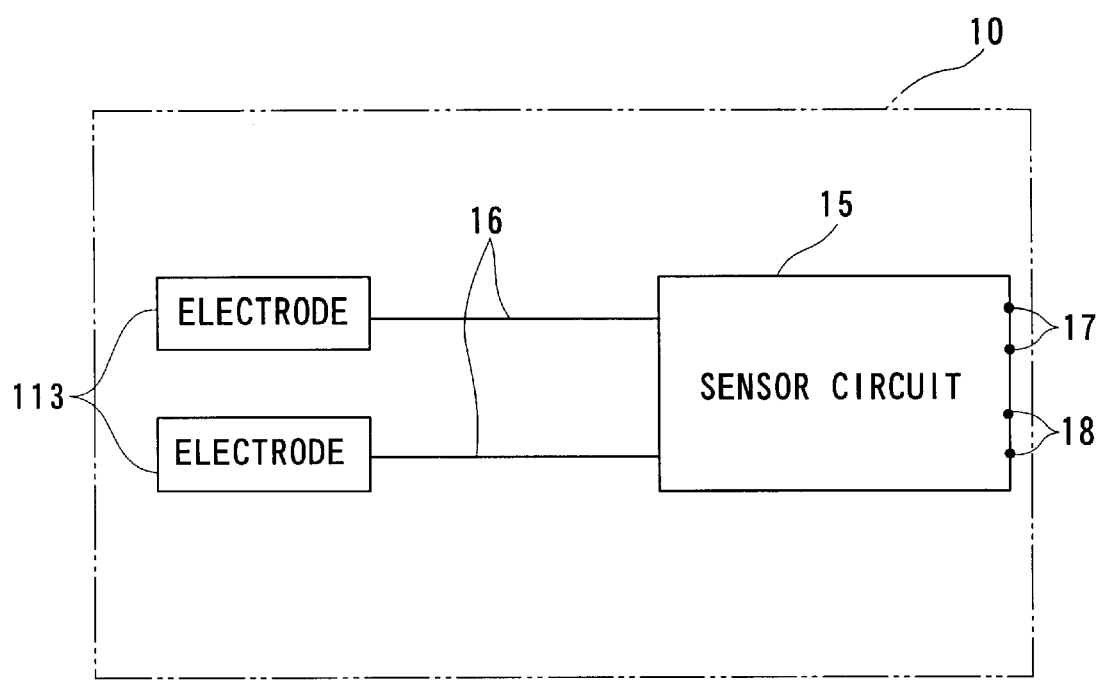

FIG. 22A
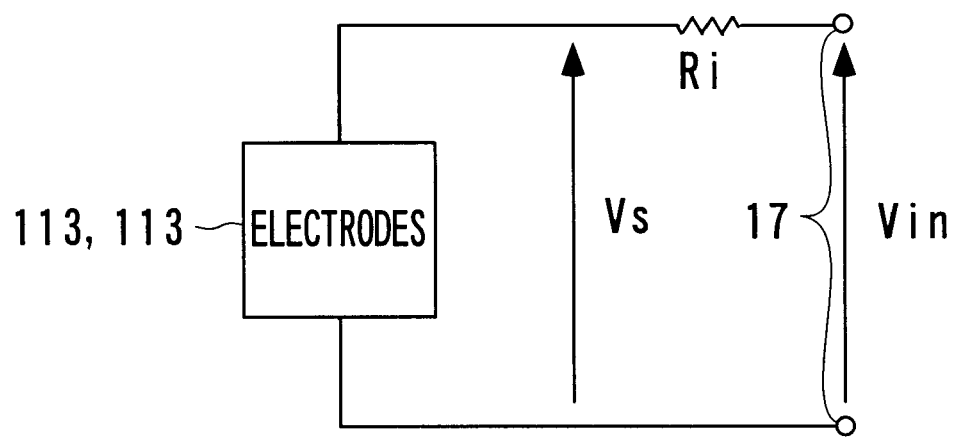
FIG. 22B
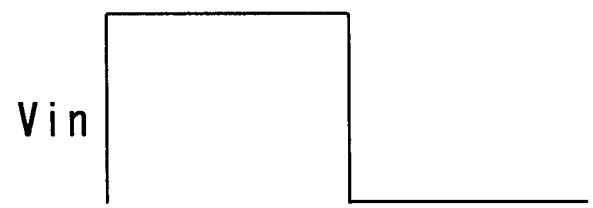
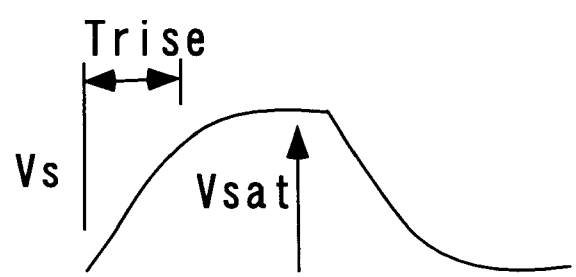

ADSORPTION AMOUNT SENSOR AND COKING SENSOR FOR INTERNAL COMBUSTION ENGINE

BACKGROUND OF THE INVENTION

1. Field of the Invention

This invention relates to an adsorption amount sensor for detecting an amount of hydrocarbons and/or an amount of water adsorbed by a zeolite of a hydrocarbon adsorber that adsorbs hydrocarbons or hydrocarbons and water in exhaust gases by using the zeolite as well as a coking sensor for an internal combustion engine, which is employed for detecting an amount of coke deposition (amount of coke or soot deposited) on inner surfaces of a pipe used in the engine.

2. Description of the Prior Art

Generally, in an exhaust system of a gasoline engine or the like, a three-way catalyst is arranged in an intermediate portion of an exhaust pipe in order to purify harmful substances (hydrocarbons, carbon monoxide and nitrogen compounds) in exhaust gases the amount of which can not be reduced sufficiently by engine modifications or EGR (exhaust gas recirculation). The three-way catalyst is heated by exhaust gasses or by using additional means, and activated at temperatures equal to or higher than a predetermined temperature (300° C., for instance), thereby purifying harmful substances flowing through the exhaust pipe by oxidation-reduction catalytic actions thereof. However, e.g. when the engine is started in a cold condition, before approximately 30 to 40 seconds have passed after the cold start of the engine, the temperature of the three-way catalyst is lower than the predetermined temperature, and the catalyst remains inactive, so that among the harmful substances, particularly hydrocarbons are emitted from the engine as they are as unburned combustible components. Therefore, in order to prevent emission of hydrocarbons into the air, there has been proposed an engine which incorporates not only the three-way catalyst but also a hydrocarbon adsorber arranged in an exhaust pipe thereof.

This hydrocarbon adsorber includes a zeolite as an adsorbent arranged therein along a direction of flow of exhaust gases. When the exhaust gases are passing through the hydrocarbon adsorber, molecules of hydrocarbons are caused to enter small pores of the zeolite, whereby hydrocarbons are adsorbed by the zeolite. Further, when the zeolite is heated by the exhaust gases to a temperature equal to or higher than a predetermined temperature (e.g. 100 to 250° C.), the zeolite desorbs hydrocarbons once adsorbed thereby. The desorbed hydrocarbons are circulated by the EGR and oxidized by the heated three-way catalyst.

As described above, in the hydrocarbon adsorber, although adsorption and desorption of hydrocarbons are repeatedly carried out by the zeolite, the amount of undesorbed hydrocarbons remaining or depositing in the zeolite by a long-term use thereof progressively increases, which results in the degradation of the zeolite, that is, a lowered adsorbing capacity of the zeolite for adsorbing hydrocarbons. If the engine is repeatedly started in such a state, an increasing amount of unadsorbed hydrocarbons is emitted into the air. Therefore, to carry out engine control for desorbing hydrocarbons (e.g. by elevating the temperature of the hydrocarbon adsorber) to cope with the degraded state of the zeolite, or to notify the driver of the degradation of the zeolite, it is required to detect an amount of hydrocarbons adsorbed by the zeolite.

Among methods of detecting the amount of hydrocarbons adsorbed by the zeolite or detecting the degradation of the zeolite, there are a method (1) using a hydrocarbon sensor, a method (2) using temperature sensors, and a method (3) based on measurement of a weight of the zeolite.

According to the method (1) using a hydrocarbon sensor, the hydrocarbon sensor is arranged at a location close to and upstream of a zeolite, and concentrations of hydrocarbons in exhaust gases flowing into the hydrocarbon adsorber are detected to thereby indirectly detect an amount of hydrocarbons adsorbed by the zeolite. According to the method (2) using temperature sensors, as proposed e.g. by Japanese Laid-Open Patent Publication (Kokai) No. 11-2115, the temperature sensors are arranged at locations upstream and downstream of the zeolite, and an amount of displacement between peaks of temperatures of the respective temperature sensors is detected, thereby detecting the degradation of the zeolite. According to the method (3) based on measurement of a weight of the zeolite, the hydrocarbon adsorber is removed from the exhaust pipe after stopping the engine, and the weight of the hydrocarbon adsorber is directly measured, whereby an amount of hydrocarbons adsorbed by the zeolite is detected based on the difference between the thus measured weight of the hydrocarbon adsorber and a weight of the same before use.

The above methods suffer from the following problems: In the method (1) using the hydrocarbon sensor, an amount of hydrocarbons adsorbed by the zeolite is indirectly detected, so that a detecting error is liable to occur with respect to an actual amount of hydrocarbons adsorbed by the zeolite. Moreover, a hydrocarbon sensor in general use has a limitation of detecting a concentration of a hydrocarbon up to approximately 100 ppm. To obtain a more accurate amount, it is required to provide a high-precision hydrocarbon sensor capable of detecting a concentration of approximately 20 ppm. However, such a high-precision hydrocarbon sensor is expensive, resulting in an increase in manufacturing costs of the whole exhaust system.

Further, in the method (2) using the temperature sensors, not the amount of hydrocarbons adsorbed by the zeolite but the degradation of the zeolite is detected, and hence it is impossible to detect an accurate amount of adsorbed hydrocarbons. In the method (3) based on measurement of a weight of the zeolite, although it is possible to accurately detect an amount of hydrocarbons adsorbed by the zeolite, as described above, it is required to remove the hydrocarbon adsorber from the exhaust pipe when the amount of adsorbed hydrocarbons is detected, which makes the detecting operation troublesome. Moreover, it is impossible to detect an amount of adsorbed hydrocarbons when the engine is in operation.

Depending on the temperature of exhaust gases, the amount of water contained in the exhaust gases is larger than the amount of hydrocarbons contained in the same. The zeolite of the hydrocarbon adsorber usually adsorbs water as well. Therefore, it is possible to detect the degradation of the zeolite by detecting the amount of water adsorbed by the zeolite. However, conventionally, similarly to the method (3), the detection of adsorbed water is carried out by measuring the weight of the zeolite. Hence, the operation for detecting the amount of adsorbed water is troublesome, and moreover it is impossible to detect an amount of adsorbed water when the engine is in operation.

In an internal combustion engine, when fuel is burned, coke or soot of the fuel contained in exhaust gases deposits on the inner wall of the exhaust pipe. When the temperature of the exhaust gases is higher than a predetermined temperature, the coke or soot is burned by the heat of the exhaust gases. However, when the temperature of exhaust gases is low, e.g. immediately after a cold start of the engine, the coke is not burned, and deposits on the inner wall of the exhaust pipe. If the engine is repeatedly started in such a condition, the coke deposits on a three-way catalyst arranged in the exhaust pipe to cause degradation of the performance of the three-way catalyst or increase the flow resistance of the exhaust pipe and the three-way catalyst to exhaust gases. Further, when a hydrocarbon adsorber is arranged in the exhaust pipe, for adsorbing unburned hydrocarbons contained in the exhaust gases, the coke can clog small pores of zeolite of the hydrocarbon adsorber used therein as an adsorbent, to cause degraded performance of the hydrocarbon adsorber. Therefore, to carry out engine control such that the temperature of the hydrocarbon adsorber is elevated to cause the deposited coke to burn, or indirectly determine the degree of degradation of the performance of the device, or further notify the driver of the state of deposition of the coke on the inner wall or inner surfaces of the exhaust pipe, it is required to detect the amount of coke deposition (amount of coke deposited) on the inner wall of the exhaust pipe.

One of conventional methods of detecting the amount of coke deposition is to remove the exhaust pipe from the engine after stopping the engine, and directly measure the weight of the exhaust pipe including the coke, to determine the amount of coke deposition from the difference between the thus measured weight and a weigh of the same before use.

Although this method is capable of accurately detecting the amount of coke deposition, it is required to remove the exhaust pipe from the engine, which is troublesome, and makes it impossible to detect the amount of coke deposition when the engine is in operation.

SUMMARY OF THE INVENTION

It is a first object of the invention to provide an adsorption amount sensor which is capable of accurately detecting an amount of hydrocarbons or water adsorbed by a zeolite of a hydrocarbon adsorber, even during operation of an internal combustion engine.

It is a second object of the invention to provide a coking sensor for an internal combustion engine, which is capable of accurately detecting an amount of coke deposition on inner surfaces of a pipe of an internal combustion engine even during operation of the engine.

To attain the first object, according to a first aspect of the invention, there is provided an adsorption amount sensor for detecting an amount of hydrocarbons adsorbed by a zeolite of a hydrocarbon adsorber that adsorbs hydrocarbons in exhaust gases by using the zeolite, the adsorption amount sensor comprising:

a plurality of electrodes arranged in the vicinity of the hydrocarbon adsorber in a manner opposed to each other and each carrying a zeolite thereon; and
hydrocarbon adsorption amount-detecting means for detecting the amount of hydrocarbons adsorbed, by using a parameter indicative of changes in at least one of a resistance value between the electrodes and an electrical capacitance between the electrodes.

According to this adsorption amount sensor (hereinafter referred to as the "hydrocarbon adsorption amount sensor" as required), the plurality of electrodes each carrying a zeolite thereon are arranged in the vicinity of the hydrocarbon adsorber having a zeolite for adsorbing hydrocarbons, in a manner opposed to each other, whereby a sensor can be constructed which includes electrodes each carrying thereon a zeolite having the same properties as those of the zeolite of the hydrocarbon adsorber. Hydrocarbons are adsorbed by the zeolites on the electrodes, whereby the resistance value and the electrical capacitance between the electrodes vary with the amount of hydrocarbons adsorbed. This makes it possible to detect the amount of hydrocarbons adsorbed by the zeolite of the hydrocarbon adsorber, by using the parameter indicative of changes in at least one of the resistance value and the electrical capacitance between the electrodes. In other words, since hydrocarbons tend to be adsorbed by the zeolite of the hydrocarbon adsorber and the zeolites on the electrodes substantially in the same manner, the amount of hydrocarbons adsorbed by the zeolites on the electrodes is detected by the hydrocarbon adsorption amount-detecting means, by using the above parameter, whereby the amount of hydrocarbons adsorbed by the zeolite of the hydrocarbon adsorber can be accurately detected or estimated. Further, differently from the conventional method based on a direct measurement of a weight of the zeolite, it is possible to easily detect an amount of hydrocarbons adsorbed by the zeolite and during operation of the engine, without removing the hydrocarbon adsorber from the exhaust pipe.

To attain the first object, according to a second aspect of the invention, there is provided an adsorption amount sensor for detecting an amount of water adsorbed by a zeolite of a hydrocarbon adsorber that adsorbs hydrocarbons and water in exhaust gases by using the zeolite, the adsorption amount sensor comprising:
a plurality of electrodes arranged in the vicinity of the hydrocarbon adsorber in a manner opposed to each other and each carrying a zeolite thereon; and
water adsorption amount-detecting means for detecting the amount of water adsorbed by the zeolite, by using a parameter indicative of changes in at least one of a resistance value between the electrodes and an electrical capacitance between the electrodes.

According to this adsorption amount sensor (hereinafter referred to as the "water adsorption amount sensor" as required), similarly to the adsorption amount sensor according to the first aspect of the invention, the plurality of electrodes each carrying a zeolite thereon are arranged in the vicinity of the hydrocarbon adsorber having a zeolite for adsorbing hydrocarbons and water, in a manner opposed to each other, whereby a sensor can be constructed which includes electrodes each carrying a zeolite having the same properties as those of the zeolite of the hydrocarbon adsorber. As a result, it becomes possible to detect the amount of water adsorbed by the zeolite of the hydrocarbon adsorber, by using the parameter indicative of changes in at least one of a resistance value and an electrical capacitance between the electrodes. This is because, similarly to the case of the adsorption amount sensor being applied to the hydrocarbon adsorption amount sensor, the resistance value and the electrical capacitance between the electrodes vary with the amount of water adsorbed by the zeolites on the electrodes, and water tends to be adsorbed by the zeolite of the hydrocarbon adsorber and the zeolites on the electrodes substantially in the same manner. Further, degradation of the zeolites can be detected by detecting the amount of water adsorbed by the zeolite of the hydrocarbon adsorber. Still further, it is possible to realize the water adsorption amount sensor as a sensor having the same construction as the hydrocarbon adsorption amount sensor, whereby the adsorption amount sensor can be used both as a hydrocarbon adsorption amount sensor and as a water adsorption amount sensor.

Preferably, the parameter is a voltage generated between the electrodes by application of a predetermined DC voltage between the electrodes.

According to this preferred embodiment of each of the first and second aspects of the invention, the voltage generated between the electrodes by application of the predetermined DC voltage between the electrodes properly reflects changes in the resistance value between the electrodes. Therefore, by using the voltage generated between the electrodes by the application of the predetermined DC voltage as a parameter, it is possible to properly detect the amount of hydrocarbons and/or the amount of water adsorbed by the zeolite of the hydrocarbon adsorber.

Preferably, the adsorption amount sensor further includes an oscillator for outputting a signal having an oscillation frequency dependent on the at least one of the resistance value between the electrodes and the electrical capacitance between the electrodes, and the parameter is the oscillation frequency of the signal.

According to this preferred embodiment of each of the first and second aspects of the invention, the signal output from the oscillator and having an oscillation frequency dependent on the at least one of the resistance value and the electrical capacitance between the electrodes properly reflects changes in the at least one of the resistance value and the electrical capacitance between the electrodes. That is, the oscillation frequency dependent on the resistance value and the electrical capacitance between the electrodes properly reflect changes in the resistance value between the electrodes and the electrical capacitance between the electrodes. Therefore, by using the oscillation frequency of the signal as the parameter, it is possible to properly detect the amount of hydrocarbons and/or the amount of water adsorbed by the zeolite of the hydrocarbon adsorber.

Preferably, the parameter is at least one of a convergence voltage value to which converges a voltage generated between the electrodes by application of a pulse voltage between the electrodes, and a convergence time.

According to this preferred embodiment of each of the first and second aspects of the invention, a voltage generated between the electrodes by the application of a voltage in the form of a pulse (hereinafter referred to as the "pulse voltage" throughout the specification and appended claims) between the electrodes converges to a predetermined convergence voltage value, and the convergence voltage value and a convergence time properly reflect the changes in the resistance value and the electrical capacitance between the electrodes. Therefore, by using at least one of the convergence voltage and the convergence time as a parameter, it is possible to properly detect the amount of hydrocarbons and/or the amount of water adsorbed by the zeolite of the hydrocarbon adsorber. It should be noted that throughout the specification and appended claims the term "convergence voltage value" is used to mean a voltage value to which converges a voltage generated between the electrodes by application of the pulse voltage to the electrodes, while the term "convergence time" is used to mean a rise time required until the voltage generated between the electrodes by the application of the pulse voltage reaches a predetermined proportion of the convergence voltage value.

Preferably, the electrodes have respective portions opposed to each other, the respective portions each having a shape of teeth of a hair comb, and mating with each other in a manner spaced from each other.

In the first aspect of the invention, for instance, the hydrocarbon adsorber is arranged within an exhaust pipe of an internal combustion engine, and the adsorption amount sensor detect the amount of hydrocarbons adsorbed from the exhaust gases from the internal combustion engine by the hydrocarbon adsorber, by using the parameter.

More preferably, the adsorption amount sensor is arranged in the exhaust pipe at a location upstream of the hydrocarbon adsorber.

In the second aspect of the invention, for instance, the hydrocarbon adsorber is arranged within an exhaust pipe of an internal combustion engine, and the adsorption amount sensor detects the amount of water adsorbed from the exhaust gases from the internal combustion engine by the hydrocarbon adsorber, by using the parameter.

More preferably, the adsorption amount sensor is arranged in the exhaust pipe at a location downstream of the hydrocarbon adsorber.

To attain the second object, according to a third aspect of the invention, there is provided a coking sensor for an internal combustion engine having a pipe, the coking sensor detecting an amount of coke deposition on inner surfaces of the pipe, the coking sensor comprising:
  a plurality of electrodes arranged within the pipe in a manner opposed to each other and each having a surface thereof coated with an insulating material; and
  coke deposition amount-detecting means for detecting the amount of coke deposition, by using a parameter indicative of changes in at least one of a resistance value between the electrodes and an electrical capacitance between the electrodes.

According to this coking sensor, the plurality of electrodes each coated with an insulating material are arranged within a pipe of the engine in a manner opposed to each other, and coke or soot deposits on the electrodes, whereby the resistance value and the electrical capacitance between the electrodes vary with the amount of coke deposited on the electrodes. This makes it possible to detect the amount of coke deposition within the pipe, by using the parameter indicative of changes in at least one of the resistance value and the electrical capacitance between the electrodes. In other words, since coke or soot tends to deposit on the inner surfaces of the pipe and the electrodes substantially in the same manner, by detecting the amount of coke deposition on the electrodes by using the above parameter, it is possible to accurately detect the amount of coke deposition on the inner surfaces of the pipe. Further, differently from the conventional method which directly measures a weight of the pipe, it is possible to easily detect an amount of coke deposition and even during operation of the engine, without removing the pipe from the engine. Moreover, since the surface of each electrode is coated with the insulating material, it is possible to positively prevent the electrodes from being short-circuited by coke or soot depositing between the electrodes.

Preferably, the parameter is a voltage generated between the electrodes by application of a predetermined DC voltage between the electrodes.

According to this preferred embodiment, the voltage generated between the electrodes by application of the predetermined DC voltage between the electrodes properly reflects changes in the resistance value between the electrodes. Therefore, by using the voltage generated between the electrodes by the application of the predetermined DC voltage as a parameter, it is possible to properly detect the amount of coke deposition on inner surfaces of the pipe.

Preferably, the coking sensor further includes an oscillator for outputting a signal having an oscillation frequency dependent on the at least one of the resistance value between the electrodes and the electrical capacitance between the electrodes, and the parameter is the oscillation frequency of the signal.

According to this preferred embodiment, the signal output from the oscillator and having an oscillation frequency dependent on the at least one of the resistance value and the electrical capacitance between the electrodes properly reflects changes in the at least one of the resistance value and the electrical capacitance between the electrodes. That is, the oscillation frequencies dependent respectively on the resistance value between the electrodes and the electrical capacitance between the electrodes properly reflect changes in the resistance value and the electrical capacitance. Therefore, by using one or both of the oscillation frequencies as a parameter, it is possible to properly detect the amount of coke deposition on the inner surfaces of the pipe.

Preferably, the parameter is at least one of a convergence voltage value to which converges a voltage generated between the electrodes by application of a pulse voltage between the electrodes, and a convergence time.

According to this preferred embodiment, the voltage generated between the electrodes by the application of the pulse voltage between the electrodes converges to a convergence voltage value, and the convergence voltage value and the convergence time properly reflect changes in the resistance value and the electrical capacitance between the electrodes. Therefore, by using at least one of the convergence voltage value and the convergence time as a parameter, it is possible to properly detect the amount of coke deposition on inner surfaces of the pipe.

The above and other objects, features, and advantages of the invention will become more apparent from the following detailed description taken in conjunction with the accompanying drawings.

BRIEF DESCRIPTION OF THE DRAWINGS

FIG. 1 is a block diagram schematically showing the arrangement of an adsorption amount sensor according to a first embodiment of the invention in a state incorporated in an exhaust pipe of an internal combustion engine, as a hydrocarbon adsorption amount sensor;

FIG. 4 is a block diagram schematically showing the arrangement of the hydrocarbon adsorption amount sensor;

FIGS. 6A and 6B are diagrams useful in explaining a method of detecting a hydrocarbon adsorption amount by using, as a parameter, a voltage between the electrodes generated by applying a predetermined DC voltage therebetween, in which:

FIG. 6A is a diagram schematically showing an equivalent circuit of the hydrocarbon adsorption amount sensor;

FIG. 6B is a graph useful in explaining the relationship between the amount of hydrocarbons adsorbed by the zeolite and a voltage generated between the electrodes;

FIGS. 7A and 7B are diagrams useful in explaining a method of detecting a hydrocarbon adsorption amount by using, as a parameter, an oscillation frequency of a signal generated by an oscillator, in which:

FIG. 7A is a diagram schematically showing an equivalent circuit of the hydrocarbon adsorption amount sensor;

FIG. 7B is a graph useful in explaining the relationship between the amount of hydrocarbons adsorbed by the zeolite and the oscillation frequency;

FIGS. 8A and 8B are diagrams useful in explaining a method of detecting a hydrocarbon adsorption amount by using, as parameters, a convergence voltage value to which converges a voltage generated between the electrodes by applying a pulse voltage therebetween and a convergence time, in which:

FIG. 8A is a diagram schematically showing an equivalent circuit of the hydrocarbon adsorption amount sensor;

FIG. 8B shows a diagram of a waveform of a pulse voltage, and a diagram of a waveform of a voltage corresponding to the pulse voltage, which is useful for explaining the relationship between the convergence voltage and the convergence time;

FIG. 18 is a block diagram schematically showing the arrangement of the coking sensor;

FIGS. 20A and 20B are diagrams useful in explaining a method of detecting a coke deposition amount by using, as a parameter, a voltage between the electrodes generated by applying a predetermined DC voltage therebetween, in which:

FIG. 20A is a diagram schematically showing an equivalent circuit of the coking sensor;

FIG. 20B is a graph useful in explaining the relationship between the amount of coke deposition within the exhaust pipe and the voltage generated between the electrodes;

FIGS. 21A and 21B are diagrams useful in explaining a method of detecting a coke deposition amount by using, as a parameter, an oscillation frequency of a signal generated by an oscillator, in which:

FIG. 21A is a diagram schematically showing an equivalent circuit of the coking sensor;

FIG. 21B is a graph useful in explaining the relationship between the amount of coke deposition within the exhaust pipe and the oscillation frequency;

FIGS. 22A and 22B are diagrams useful in explaining a method of detecting a coke deposition amount using, as parameters, a convergence voltage value to which converges a voltage generated between the electrodes by applying a pulse voltage therebetween and a convergence time;

FIG. 22A is a diagram schematically showing an equivalent circuit of the coking sensor;

FIG. 22B shows a diagram of a waveform of a pulse voltage, and a diagram of a waveform of a voltage corresponding to the pulse voltage, which is useful for explaining the relationship between the convergence voltage and the convergence time.

DETAILED DESCRIPTION

Figure 2A:
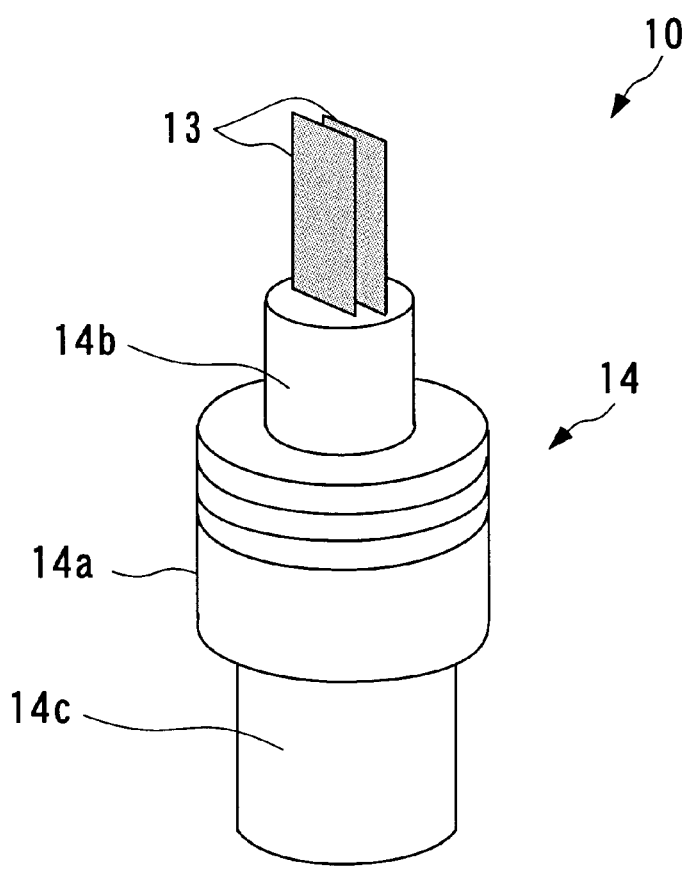
FIG. 2A is a perspective view showing an appearance of the hydrocarbon adsorption amount sensor.

The invention will now be described in detail with reference to the drawings showing embodiments thereof.

Referring first to FIG. 1, there is schematically shown the arrangement of an internal combustion engine having an adsorption amount sensor according to a first embodiment of the invention inserted into an exhaust pipe of the engine as a hydrocarbon adsorption amount sensor. As shown in the figure, the exhaust pipe 2 for discharging exhaust gases out of the internal combustion engine 1 is connected to the engine 1 via an exhaust manifold, not shown. A three-way catalyst 3 is arranged in an intermediate portion of the exhaust pipe 2, and a hydrocarbon adsorber 4 at a location downstream of the three-way catalyst 3 in the exhaust pipe 2, for adsorbing hydrocarbons as unburned combustible components in exhaust gases. Further, arranged at a location immediately upstream of the hydrocarbon adsorber 4 in an intermediate portion of the exhaust pipe 2 is a hydrocarbon adsorption amount sensor 10 (adsorption amount sensor) for detecting an amount of hydrocarbons adsorbed by a zeolite 12, referred to hereinafter, of the hydrocarbon adsorber 4. The hydrocarbon adsorption amount sensor 10 and the internal combustion engine 1 are electrically connected to an ECU 11, which notifies the driver of results of detection carried out by the hydrocarbon adsorption amount sensor 10, and controls the internal combustion engine 1.

The three-way catalyst 3 is heated by the heat of exhaust gasses and activated at a temperature equal to or higher than a predetermined temperature (300° C., for instance), thereby purifying harmful substances (hydrocarbons, carbon monoxide and nitrogen compounds) in exhaust gases emitted from the internal combustion engine 1 by performing oxidation-reduction catalytic actions. However, the three-way catalyst 3 is not activated before approximately 30 to 40 seconds have passed after a cold start of the engine 1. Therefore, in order to prevent hydrocarbons among the harmful substances from being emitted from the engine 1 as unburned combustible components, hydrocarbons passed through the three-way catalyst 3 are adsorbed by the hydrocarbon adsorber 4.

The hydrocarbon adsorber 4 includes the zeolite 12 as a hydrocarbon adsorbent, arranged in a direction of outflow of exhaust gases. The zeolite 12 has a surface formed with a lot of small pores, not shown, which permit hydrocarbon molecules to enter the same, thereby adsorbing hydrocarbons. Further, the zeolite 12 desorbs hydrocarbons once adsorbed thereby when it is heated by exhaust gases to a temperature equal to or higher than a predetermined temperature (e.g. 100 to 250° C.).

Figure 2B:
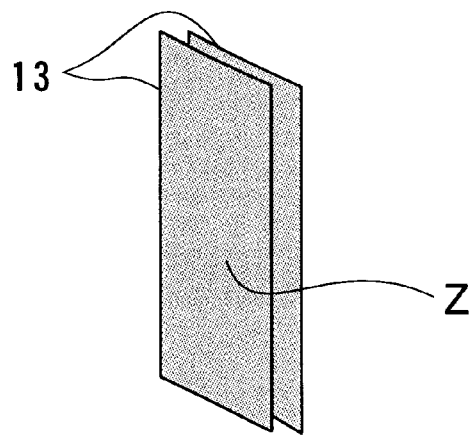
FIG. 2B is a perspective view showing an appearance of electrodes appearing in FIG. 2A.

Referring to FIGS. 2A and 2B, the hydrocarbon adsorption amount sensor 10 includes a pair of electrodes 13 and 13 arranged such that they are opposed to each other with a predetermined gap therebetween, an electrode-supporting member 14 for supporting the electrodes 13 and 13, and a sensor circuit 15 (hydrocarbon adsorption amount-detecting means, see FIG. 4) contained in the electrode-supporting member 14. Each electrode 13 is formed of an electrically conductive and heat-resistant material, such as a copper alloy plate, and carries a zeolite Z having the same properties as those of the zeolite 12 of the above hydrocarbon adsorber 4, on a surface thereof. To cause the electrode 13 to carry the zeolite Z thereon, the electrode 13 is immersed in the zeolite Z in liquid form to have its surface coated with the zeolite Z.

Figure 3:
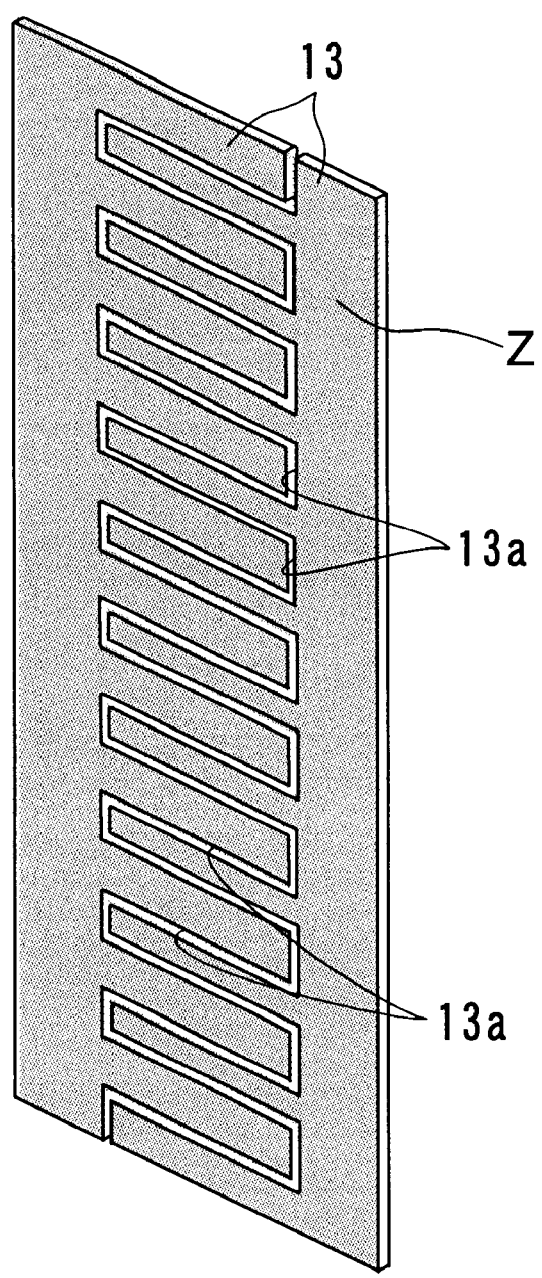
FIG. 3 is a perspective view showing an appearance of electrodes each formed differently from the FIG. 2B electrodes to have a comb teeth-like shape.

As shown in FIG. 3, each of the pair of electrodes 13 and 13 may be formed to have a hair comb-like shape. In this case, opposed portions of the respective electrodes 13 are formed to have a shape of teeth of a hair comb, and the electrodes 13 and 13 are arranged on a substrate, not shown, formed of a heat-resistant insulating material, such that the teeth-shaped portions mate with each other and at the same time spaced from each other by a predetermined distance such that the opposed mating portions are not in contact with each other. Further, in forming the hair comb-shaped electrodes 13 and 13 arranged as above, a metal plate having a rectangular shape is rigidly fixed to the above substrate, and after a zeolite Z is caused to be carried on a surface of the metal plate, a gap 13a shown in FIG. 3 may be formed by etching. The hair comb-shaped electrodes 13 and 13 can be produced very easily by this method.

The whole of the electrode-supporting member 14 is formed of a heat-resistant material. As shown in FIGS. 2A and 2B, the electrode-supporting member 14 is comprised of a hollow cylindrical main block 14a containing the sensor circuit 15, a columnar supporting block 14b arranged on the top of the main block 14a in a manner protruding therefrom and having lower ends of the electrodes 13 and 13 rigidly fixed thereto for supporting the electrodes 13 and 13, and a columnar connecting block 14c protruding from the bottom of the main block 14a and having a connecting port, not shown, extending therethrough for electrically connecting terminals of the sensor circuit 15 to the above-mentioned ECU 11. The electrodes 13 and 13 supported by the supporting block 14b are electrically connected to the sensor circuit 15 in the main block 14a via two connecting lines 16 and 16 extending through the supporting block 14b, as shown in FIG. 4.

The sensor circuit 15 includes a pair of input terminals 17 and 17 and a pair of output terminals 18 and 18, each of which is electrically connected to the ECU 11. The sensor circuit 15 is configured such that when a predetermined voltage, referred to hereinafter, is applied to the input terminals 17 and 17, an electrical signal indicative of a parameter, referred to hereinafter, indicating changes in at least one of a resistance value and an electrical capacitance between the electrodes 13 and 13 is output from the output terminals 18.

The hydrocarbon adsorption amount sensor 10 constructed as above is attached to the exhaust pipe 2 such that the electrodes 13 and 13 and the supporting block 14b are inserted into the exhaust pipe 2.

Figure 5A:
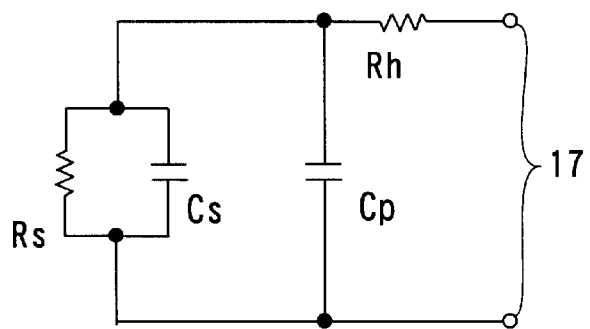
FIG. 5A is an equivalent circuit of the hydrocarbon adsorption amount sensor.
Figure 5B:
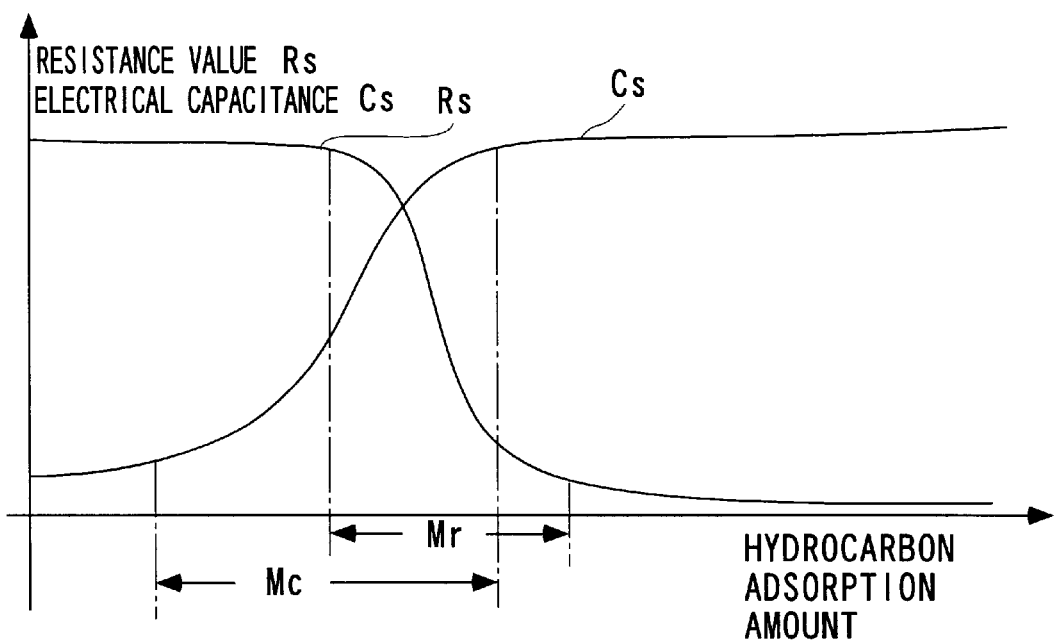
FIG. 5B is a graph useful in explaining the relationship between an amount of hydrocarbons adsorbed by a zeolite, and a resistance value and an electrical capacitance between the electrodes.

FIG. 5A shows an equivalent circuit of the hydrocarbon adsorption amount sensor 10. When the predetermined voltage is applied between the input terminals 17 and 17 in the figure, the resistance value Rs and the electrical capacitance Cs between the electrodes 13 and 13 vary, as shown in FIG. 5B, with the amount of hydrocarbons adsorbed by the zeolite Z on the electrodes 13. More specifically, the resistance value Rs progressively decreases as the amount of hydrocarbons adsorbed by the zeolite Z increases, and it sharply decreases when the amount of adsorbed hydrocarbons lies within a predetermined range Mr, but it again progressively decreases after the amount of adsorbed hydrocarbons exceeds the predetermined range Mr. On the other hand, the electrical capacitance Cs progressively increases as the amount of hydrocarbons adsorbed by the zeolite Z increases, and it sharply increases when the amount of adsorbed hydrocarbons lies within a predetermined range Mc, but it again progressively increases after the amount of adsorbed hydrocarbons exceeds the predetermined range Mc.

It should be noted that the hydrocarbon adsorption amount sensor 10 is configured such that the resistance value Rs and the electrical capacitance Cs between the electrodes 13 and 13 are far larger than a resistance value Rh of a harness in the sensor circuit 15 and a parasitic capacitance Cp by the harness. Accordingly, the resistance value Rs and the electrical capacitance Cs between the electrodes 13 and 13 vary with the amount of hydrocarbons adsorbed by the zeolite Z on the electrodes 13 and 13, without being affected by the resistance value Rh and the parasitic capacitance Cp.

According to the hydrocarbon adsorption amount sensor 10 configured as above, the electrodes 13 and 13 carrying the zeolite Z thereon are arranged at a location close to the hydrocarbon adsorber 4 in a manner opposed to each other, whereby it is possible to construct a sensor which has electrodes carrying the zeolite Z having the same properties as those of the zeolite 12 of the hydrocarbon adsorber 4. As described above, hydrocarbons are adsorbed by the zeolite Z on the electrodes 13 and 13, so that the resistance value Rs and the electrical capacitance Cs between the electrodes 13 and 13 vary with the amount of hydrocarbons adsorbed. This makes it possible to detect the amount of hydrocarbons adsorbed by the zeolite 12 of the hydrocarbon adsorber 4, by using the parameter indicative of changes in at least one of the resistance value Rs and the electrical capacitance Cs between the electrodes 13 and 13. In other words, since hydrocarbons tend to be adsorbed by the zeolite 12 of the hydrocarbon adsorber 4 and the zeolite Z on the electrodes 13 and 13 substantially in the same manner, the amount of hydrocarbons adsorbed by the zeolite Z on the electrodes 13 and 13 can be detected by the sensor circuit 15 by using the parameter, whereby the amount of hydrocarbons adsorbed by the zeolite 12 of the hydrocarbon adsorber 4 can be accurately detected or estimated. Further, differently from the conventional method of directly measuring a weight of the zeolite 12, it is possible to easily detect an amount of hydrocarbons adsorbed (hydrocarbon adsorption amount) and during operation of the internal combustion engine 1, without removing the hydrocarbon adsorber 4 from the exhaust pipe 2.

As shown in FIG. 5B, the predetermined ranges Mr and Mc of the hydrocarbon adsorption amount, within which the resistance value Rs and the electrical capacitance Cs between the electrodes 13 and 13 sharply change with the hydrocarbon adsorption amount, are not coincident with each other but partially overlapping each other. Therefore, the hydrocarbon adsorption amount can be detected by using both the resistance value Rs and the electrical capacitance Cs between the electrodes 13 and 13, whereby it is possible to detect a wider range of the hydrocarbon adsorption amount with higher accuracy than when the hydrocarbon adsorption amount is detected by using only one of the resistance value Rs and the electrical capacitance Cs.

Next, methods of detecting the hydrocarbon adsorption amount by using several kinds of parameters based on the resistance value Rs and the electrical capacitance Cs between the electrodes 13 and 13 will be described with reference to FIGS. 6A to 9. In the following, (1) a method using a voltage between the electrodes as a parameter, (2) a method using an oscillation frequency of a signal generated by an oscillator as a parameter, and (3) a method using a convergence voltage value to which converges a voltage between electrodes and a convergence time as parameters, will be described, one by one.

(1) Method Using a Voltage Between the Electrodes as a Parameter

Figure 6A:
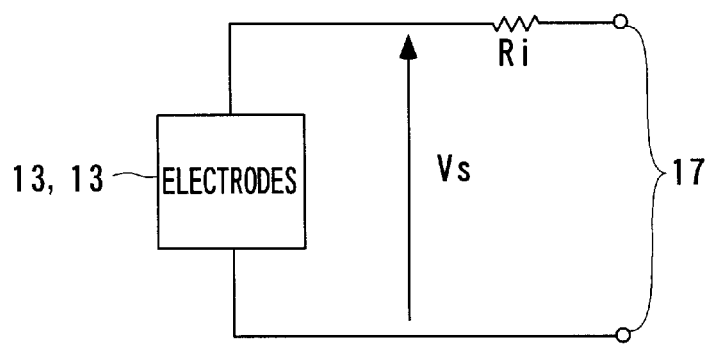
Figure 6B:
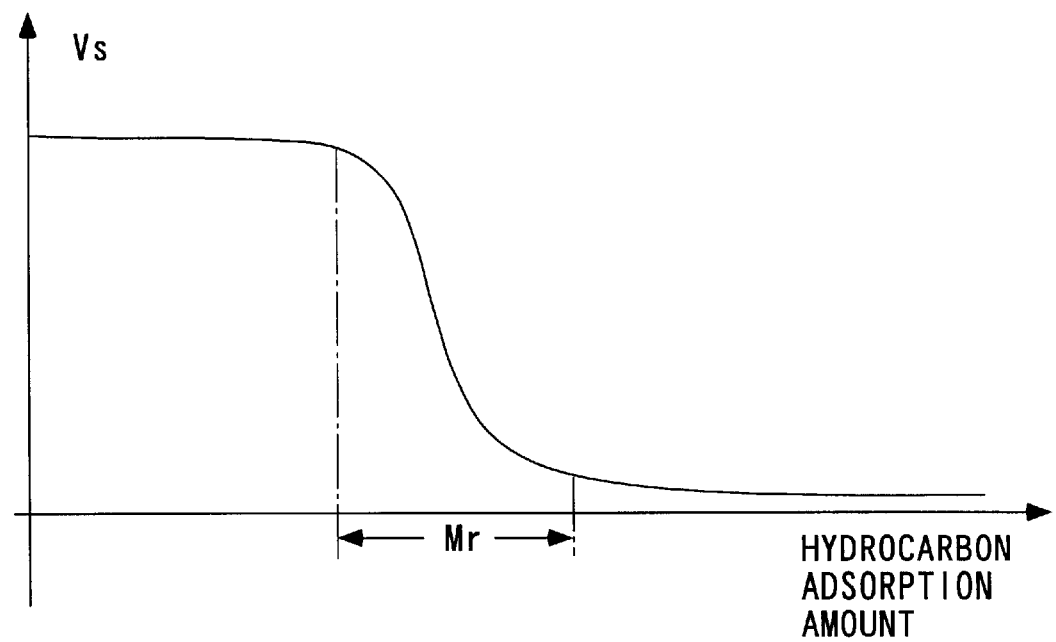

FIG. 6A schematically shows an equivalent circuit of the hydrocarbon adsorption amount sensor 10 employing the method using a voltage generated between the electrodes 13 and 13 by applying a predetermined DC voltage therebetween. In this case, the electrodes 13 and 13 function as a resistance. Ri in the figure designates a resistance arranged in the sensor circuit 15, which is connected in series with the electrodes 13 and 13. In the circuit constructed as above, when the predetermined DC voltage is applied between the electrodes 13 and 13 via the input terminals 17 and 17, the voltage Vs generated between the electrodes 13 and 13 decreases as the amount of hydrocarbons adsorbed by the zeolite Z on the electrodes 13 and 13 increases. More specifically, as shown in FIG. 6B, the voltage Vs progressively decreases as the amount of hydrocarbons adsorbed by the zeolite Z on the electrodes 13 and 13 increases, and it sharply decreases when the amount of adsorbed hydrocarbons lies within the predetermined range Mr. The voltage Vs again progressively decreases after the amount of adsorbed hydrocarbons exceeds the predetermined range Mr.

In other words, changes in the voltage Vs generated between the electrodes 13 and 13 by application of the above predetermined DC voltage between the electrodes 13 and 13 approximately agree with changes in the resistance value Rs between the electrodes 13 and 13 and properly reflect the changes in the resistance value Rs. Therefore, the amount of hydrocarbons adsorbed by the zeolite 12 of the hydrocarbon adsorber 4 can be properly detected or estimated by using, as a parameter, the voltage Vs generated between the electrodes 13 and 13 through the application of the predetermined DC voltage.

Figure 7A:
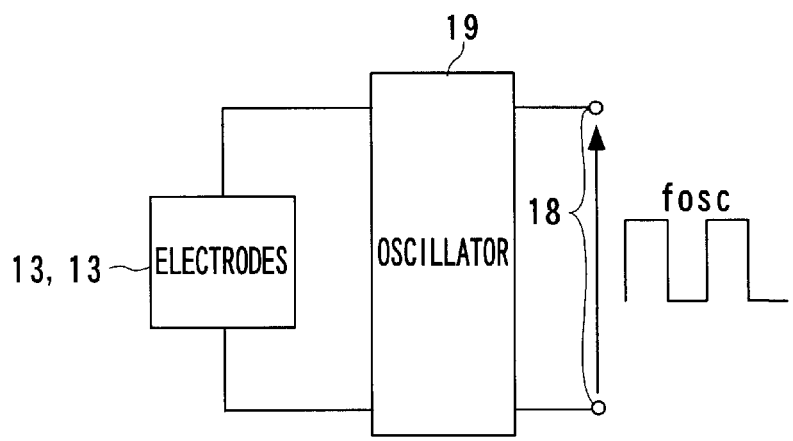
Figure 7B:
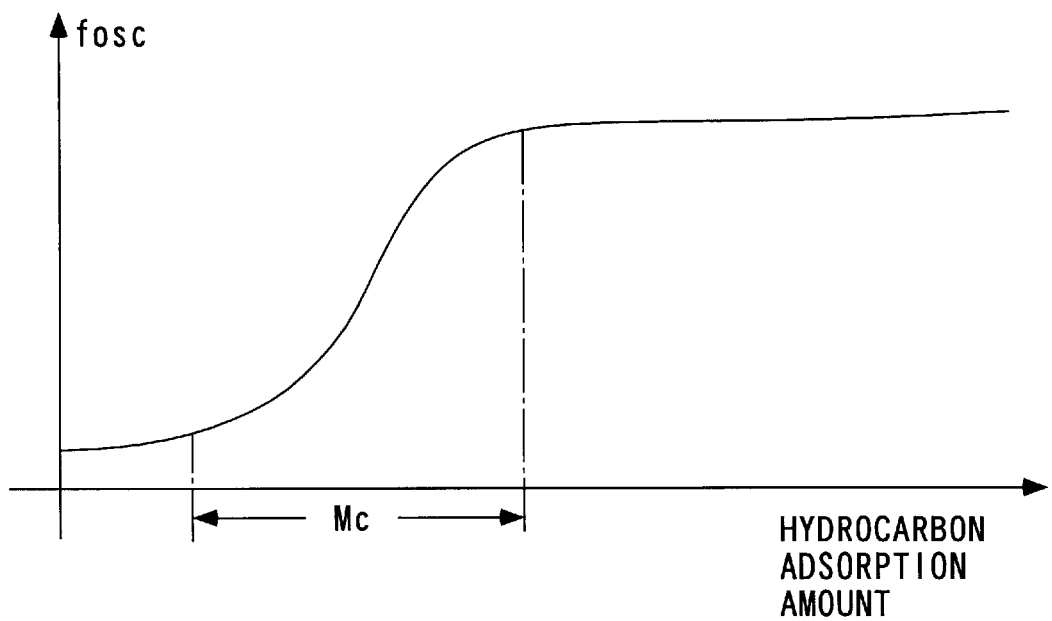

(2) Method Using an Oscillation Frequency of a Signal Generated by an Oscillator as a Parameter FIG. 7A schematically shows an equivalent circuit of the hydrocarbon adsorption amount sensor 10, in which the oscillator 19 is incorporated in the sensor circuit 15. The oscillator 19 is configured such that a signal having an oscillation frequency fosc dependent on the electrical capacitance Cs between the electrodes 13 and 13 is output from the output terminals 18 and 18. In the circuit constructed as above, the oscillation frequency fosc of the signal generated by the oscillator 19 increases as the amount of hydrocarbons adsorbed by the zeolite Z on the electrodes 13 and 13 increases. More specifically, as shown in FIG. 7B, the oscillation frequency fosc progressively increases as the amount of hydrocarbons adsorbed by the zeolite Z on the electrodes 13 and 13 increases, and it sharply increases when the amount of adsorbed hydrocarbons lies within the predetermined range Mc. The oscillation frequency fosc again progressively increases after the amount of adsorbed hydrocarbons exceeds the predetermined range Mc.

In other words, changes in the oscillation frequency fosc of the signal generated by the oscillator 19 approximately agree with changes in the electrical capacitance Cs between the electrodes 13 and 13, and properly reflect the changes in the electrical capacitance Cs. Therefore, the amount of hydrocarbons adsorbed by the zeolite 12 of the hydrocarbon adsorber 4 can be properly detected or estimated by using the oscillation frequency fosc as a parameter.

The above oscillator 19 is not limited to one which outputs a signal having an oscillation frequency dependent on the electrical capacitance Cs between the electrodes 13 and 13, but the oscillator 19 may be configured such that it outputs a signal having an oscillation frequency dependent on the resistance value Rs between the electrodes 13 and 13, in place of or in combination with the signal having the oscillation frequency dependent on the electrical capacitance Cs. In this case, changes in the oscillation frequency approximately agree with changes in the resistance value Rs between the electrodes 13 and 13, and properly reflect the changes in the resistance value Rs. Therefore, the amount of hydrocarbons adsorbed by the zeolite 12 of the hydrocarbon adsorber 4 can be further properly detected or estimated. Further, the oscillator may be provided outside the sensor circuit 15, for instance, within the ECU 11.

Figure 9:
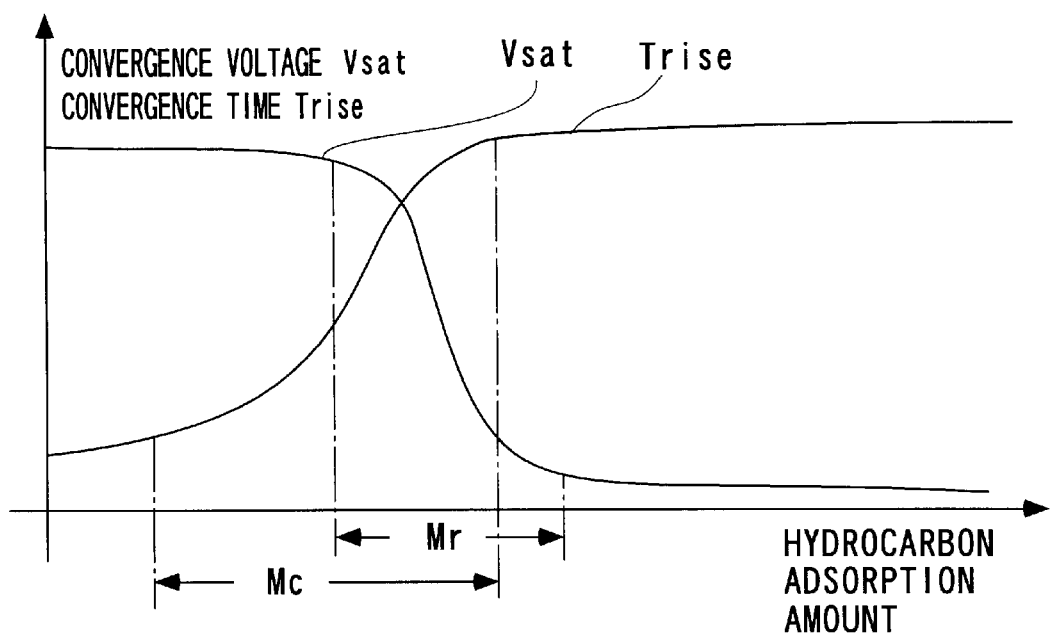
FIG. 9 is a graph useful in explaining the relationship between the amount of hydrocarbons adsorbed by the zeolite and the convergence voltage value/convergence time, in the case of the pulse voltage being applied between the electrodes.

(3) Method Using a Convergence Voltage Value and a Convergence Time as Parameters FIG. 8A schematically shows an equivalent circuit of the hydrocarbon adsorption amount sensor 10 employing the method using a convergence voltage value and a convergence time measured by applying a predetermined rectangular pulse voltage Vin between the electrodes 13 and 13. In the circuit constructed as shown in FIG. 8A, when the predetermined pulse voltage Vin is applied between the electrodes 13 and 13 via the input terminals 17 and 17, a voltage Vs generated between the electrodes 13 and 13 converges to a convergence voltage value Vsat dependent on the amount of hydrocarbons adsorbed by the zeolite Z on the electrodes 13 and 13. The convergence voltage value Vsat of the voltage Vs decreases as the amount of hydrocarbons adsorbed by the zeolite Z on the electrodes 13 and 13 increases. More specifically, as shown in FIG. 9, the convergence voltage value Vsat progressively decreases as the amount of hydrocarbons adsorbed by the zeolite Z on the electrodes 13 and 13 increases, and it sharply decreases when the amount of adsorbed hydrocarbons lies within the predetermined range Mr. The convergence voltage value Vsat again progressively decreases after the amount of adsorbed hydrocarbons exceeds the predetermined range Mr. On the other hand, the convergence time Trise increases as the amount of hydrocarbons adsorbed by the zeolite Z on the electrodes 13 and 13 increases. More specifically, as shown in FIG. 9, the convergence time Trise progressively increases as the amount of hydrocarbons adsorbed by the zeolite Z on the electrodes 13 and 13 increases, and it sharply increases when the amount of adsorbed hydrocarbons lies within the predetermined range Mc. The convergence time Trise again progressively increases after the amount of adsorbed hydrocarbons exceeds the predetermined range Mc.

In other words, changes in the convergence voltage value Vsat to which converges the voltage Vs generated between the electrodes 13 and 13 upon application of the above predetermined pulse voltage to the electrodes 13 and 13 and the convergence time Trise approximately agree with the changes in the resistance value Rs and the electrical capacitance Cs between the electrodes 13 and 13, and properly reflect the changes in the resistance value Rs and the electrical capacitance Cs. Therefore, the amount of hydrocarbons adsorbed by the zeolite 12 of the hydrocarbon adsorber 4 can be properly detected or estimated by using at least one of the convergence voltage value Vsat and the convergence time Trise as a parameter.

Although in the above first embodiment, the hydrocarbon adsorption amount sensor 10 is arranged at a location upstream of the hydrocarbon adsorber 4, this is not limitative, but the same may be arranged at a location downstream of the hydrocarbon adsorber 4. Further, the electrodes 13 of the hydrocarbon adsorption amount sensor 10 may be comprised of three or more electrodes. In this case, the amount of hydrocarbons adsorbed by the zeolite Z on the electrodes 13 can be detected more accurately, thereby making it possible to detect or estimate the amount of hydrocarbons adsorbed by the zeolite 12 of the hydrocarbon adsorber 4 with higher accuracy.

Next, an adsorption amount sensor according to a second embodiment of the invention, which is applied to a water adsorption amount sensor, will be described with reference to FIGS. 10 to 14. It should be noted that in the following description, component parts and elements similar to those of the first embodiment are designated by identical reference numerals, and detailed description thereof is omitted.

Figure 10:
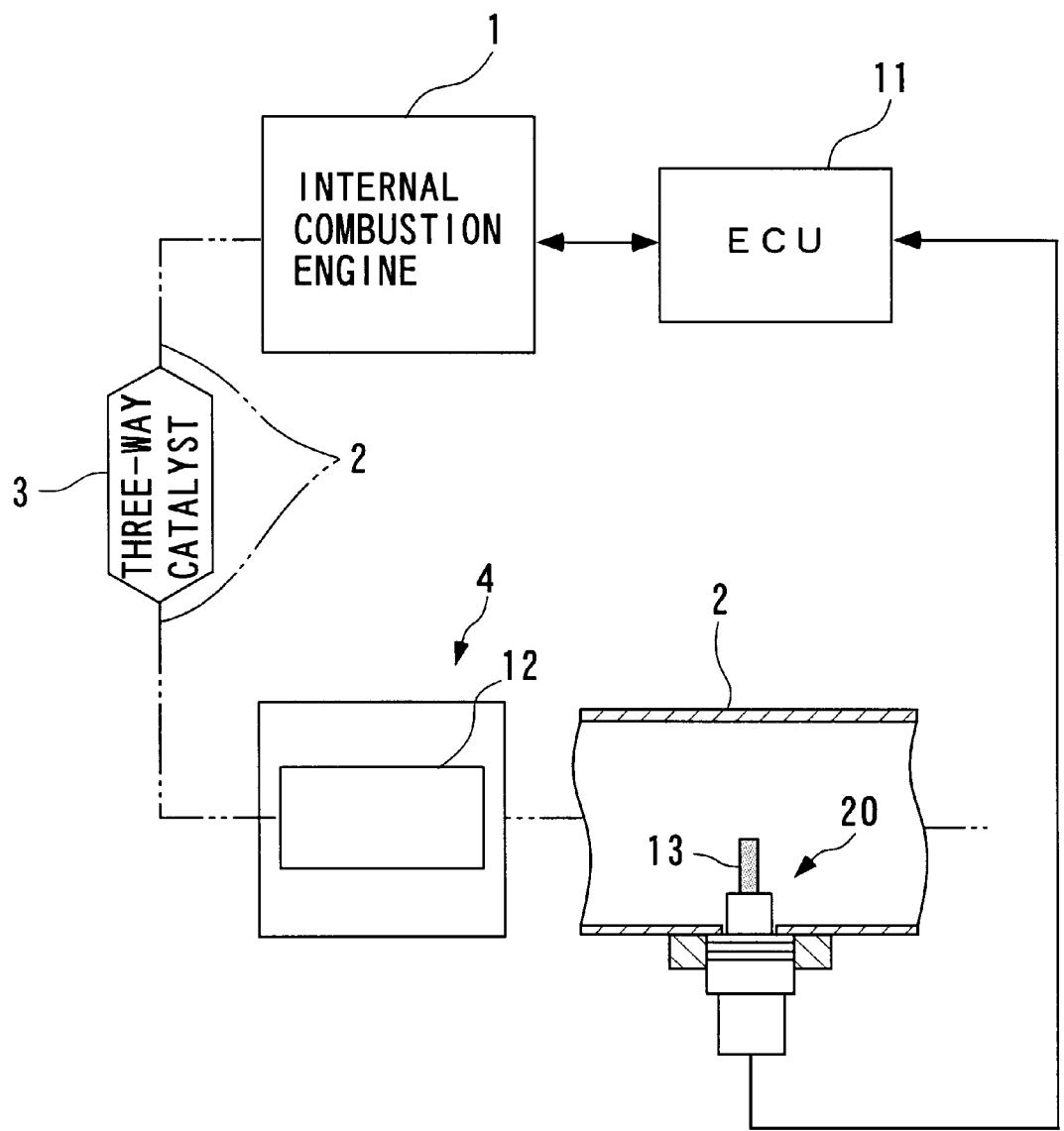
FIG. 10 is a block diagram schematically showing the arrangement of an adsorption amount sensor according to a second embodiment of the invention in a state incorporated in an exhaust pipe of an internal combustion engine, as a water adsorption amount sensor.

As shown in FIG. 10, a three-way catalyst 3 and a hydrocarbon adsorber 4 including a zeolite 12 are arranged at respective intermediate portions of an exhaust pipe 2 connected to an internal combustion engine 1, sequentially in a direction of outflow of exhaust gases. Further, a water adsorption amount sensor 20 is arranged at a location immediately downstream of the hydrocarbon adsorber 4. The water adsorption amount sensor 20 is provided for detecting an amount of water adsorbed from exhaust gases by the zeolite 12 of the hydrocarbon adsorber 4, and constructed similarly to the hydrocarbon adsorption amount sensor 10 described hereinabove. More specifically, similarly to the hydrocarbon adsorption amount sensor 10, the water adsorption amount sensor 20 includes a pair of electrodes 13 and 13, an electrode-supporting member 14, and a sensor circuit 15 (water adsorption amount-detecting means) (see FIGS. 2A, 2B and 4). Each electrode 13 carries a zeolite Z having the same properties as those of the zeolite 12 of the above hydrocarbon adsorber 4, on a surface thereof. Further, as shown in FIG. 10, the water adsorption amount sensor 20 is attached to the exhaust pipe 2 in a manner such that the electrodes 13 and 13 and a supporting block 14b thereof are inserted into the exhaust pipe 2.

Figure 11:
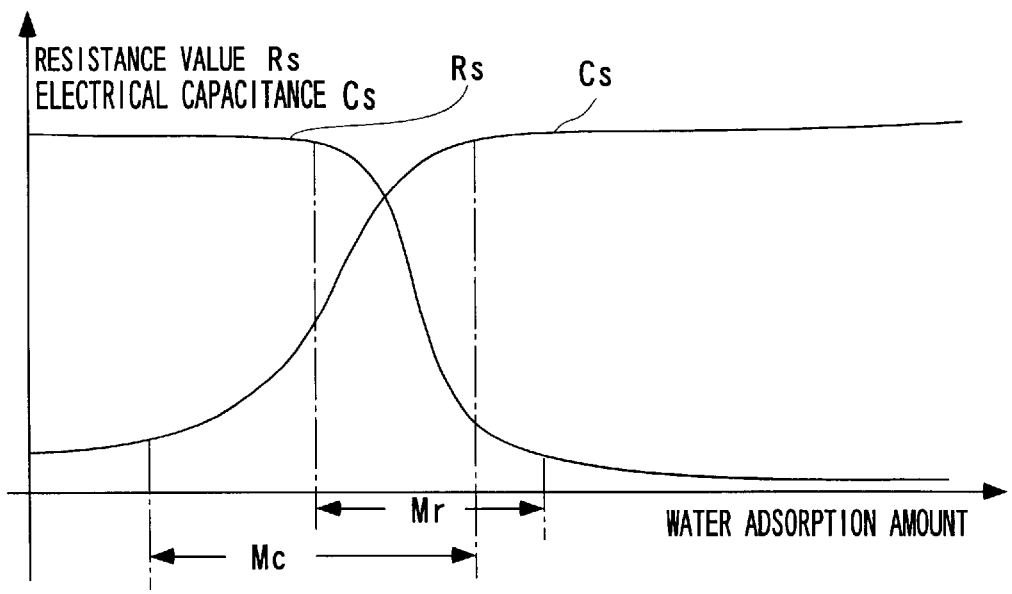
FIG. 11 is a graph useful in explaining the relationship between the amount of water adsorbed by the zeolite and a resistance value and an electrical capacitance between the electrodes.

Similarly to the hydrocarbon adsorption amount sensor 10, the water adsorption amount sensor 20 can be represented by the equivalent circuit shown in FIG. 5A. When a predetermined voltage is applied to input terminals 17 and 17 in the figure, a resistance value Rs and an electrical capacitance Cs between the electrodes 13 and 13 vary, as shown in FIG. 11, with the amount of water adsorbed by the zeolite Z on the electrode 13. More specifically, the resistance value Rs progressively decreases as the amount of water adsorbed by the zeolite Z increases, and it sharply decreases when the amount of adsorbed water lies within a predetermined range Mr. After the amount of adsorbed water exceeds the predetermined range Mr, the resistance value Rs again progressively decreases. On the other hand, the electrical capacitance Cs progressively increases as the amount of water adsorbed by the zeolite Z increases, and it sharply increases when the amount of adsorbed water lies within a predetermined range Mc, but it again progressively increases after the amount of adsorbed water exceeds the predetermined range Mc.

As described above, similarly to the resistance value Rs and the electrical capacitance Cs dependent on the hydrocarbon adsorption amount in the case of the hydrocarbon adsorption amount sensor 10, the resistance value Rs and the electrical capacitance Cs between the electrodes 13 and 13 in the water adsorption amount sensor 20 vary with the amount of water adsorbed by the zeolite Z on the electrodes 13, as is clear from comparison of FIG. 11 with FIG. 5A. Moreover, the resistance value Rs and the electrical capacitance Cs of the sensor 10 and those of the sensor 20 show the same changing characteristics. The water adsorption amount sensor 20 is thus constructed because water tends to be adsorbed by the zeolite 12 of the hydrocarbon adsorber 4 and the zeolite Z on the electrodes 13 substantially in the same manner, similarly to hydrocarbons to be detected by the adsorption amount sensor applied to the hydrocarbon adsorption amount sensor 10. Therefore, the water adsorption amount sensor 20 constructed as above is arranged at a location close to the hydrocarbon adsorber 4, whereby it is possible to accurately detect the amount of water adsorbed by the zeolite 12 of the hydrocarbon adsorber 4, by using the parameter indicative of changes in at least one of the resistance value Rs and the electrical capacitance Cs between the electrodes 13 and 13.

Generally, when the temperature of exhaust gases is low (lower than e.g. 100° C.), e.g. immediately after a cold start of the engine, the amount of water contained in the exhaust gases is larger than the amount of hydrocarbons contained in the same, whereas when the temperature of exhaust gases is high, the amount of hydrocarbons contained in the exhaust gases is larger than the amount of water contained in the same. Therefore, if a temperature sensor for detecting the temperature of exhaust gases, a gas sensor for detecting components of exhaust gases, or the like is arranged at a location close to the adsorption amount sensor according to the invention, it is possible to identify a principal component of exhaust gases and employ the adsorption amount sensor as a hydrocarbon adsorption amount sensor or a water adsorption amount sensor. In short, a single adsorption amount sensor can be used both as a hydrocarbon adsorption amount sensor and as a water adsorption amount sensor. When the adsorption amount sensor is applied to a hydrocarbon adsorption amount sensor, the amount of hydrocarbons adsorbed by the zeolite 12 of the hydrocarbon adsorber 4 can be detected or estimated, whereas when the adsorption amount sensor is applied to a water adsorption amount sensor, the amount of water adsorbed by the zeolite 12 can be detected or estimated. Of course, also when hydrocarbons and water are contained as a mixture in exhaust gases, it is possible to utilize the adsorption amount sensor as a sensor for detecting or estimating the amounts of both of the hydrocarbons and the water. If the amounts of hydrocarbons and water adsorbed by the zeolite 12 are detected or estimated in the above manners, degradation of the zeolite 12 can be detected.

Further, it is considered that water-adsorbing capacity and hydrocarbon-adsorbing capacity of the zeolite 12 of the hydrocarbon adsorber 4 are in a proportional relationship, so that especially when the water adsorption amount sensor 20 is arranged at a location downstream of the hydrocarbon adsorber 4 as in the present embodiment, it is possible to suitably detect the degradation of the zeolite 12. More specifically, if the zeolite 12 of the hydrocarbon adsorber 4 is not degraded, a large amount of water in exhaust gases is adsorbed by the zeolite 12, and it will be determined by the water adsorption amount-sensor 20 that exhaust gases passed through the hydrocarbon adsorber 4 contain a small amount of water. As a result of the determination, it is possible to estimate that the zeolite 12 of the hydrocarbon adsorber 4 is not degraded, since the zeolite adsorbs not only the water but also a large amount of hydrocarbons. On the other hand, if the zeolite 12 of the hydrocarbon adsorber 4 is degraded, the zeolite 12 does not adsorb a large amount of water from exhaust gases, so that it will be determined by the water adsorption amount sensor 20 that exhaust gases passed through the hydrocarbon adsorber 4 contain a large amount of water. As a result of the determination, it is possible to estimate that the zeolite 12 is degraded, since the zeolite 12 adsorbs neither the large amount of water nor a large amount of hydrocarbons. Accordingly, as described above, especially in the present embodiment in which the water adsorption amount sensor 20 is arranged at a location downstream of the hydrocarbon adsorber 4, it is possible to suitably detect the degradation of the zeolite 12 of the hydrocarbon adsorber 4.

In the present embodiment, similarly to the first embodiment, changes in the resistance value Rs and the electrical capacitance Cs between the electrodes 13 and 13 can also be detected by using (1) a voltage between the electrodes, (2) an oscillation frequency of a signal generated by an oscillator, and (3) a convergence voltage value to which converges a voltage between electrodes and a convergence time, as parameters. In the following, the methods using these parameters will be briefly described one by one with reference to FIGS. 12 to 14.

(1) Method Using the Voltage Between Electrodes as the Parameter

Figure 12:
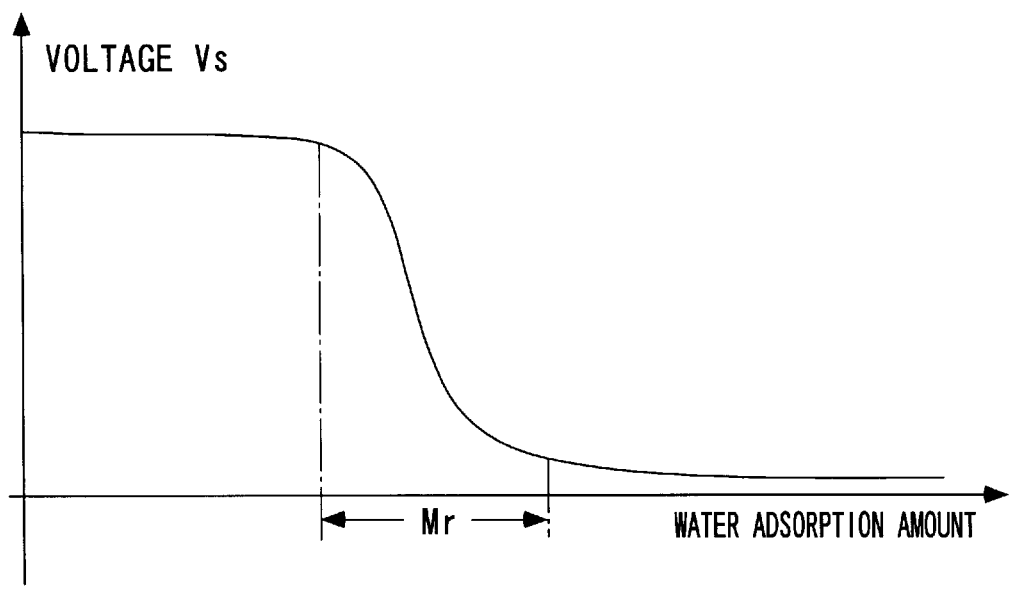
FIG. 12 is a graph which is useful in explaining a method of detecting a water adsorption amount by using, as a parameter, a voltage generated between the electrodes by applying a predetermined DC voltage therebetween, and which shows the relationship between the amount of water adsorbed by the zeolite and the voltage generated between the electrodes.

A graph shown in FIG. 12, corresponding to the FIG. 6B graph referred to hereinabove in the first embodiment, shows that a voltage Vs generated between the electrodes 13 and 13 by applying a predetermined DC voltage between the electrodes 13 and 13 decreases as the amount of water adsorbed by the zeolite Z on the electrodes 13 and 13 increases (see FIG. 6A for an equivalent circuit of the water adsorption amount sensor 20). Thus, changes in the voltage Vs generated between the electrodes 13 and 13 by application of the predetermined DC voltage between the electrodes 13 and 13 approximately agree with changes in the resistance value Rs between the electrodes 13 and 13 and properly reflect the changes in the resistance value Rs. Therefore, the amount of water adsorbed by the zeolite 12 of the hydrocarbon adsorber 4 can be properly detected or estimated by using, as a parameter, the voltage Vs generated between the electrodes 13 and 13 through the application of the predetermined DC voltage.

Figure 13:
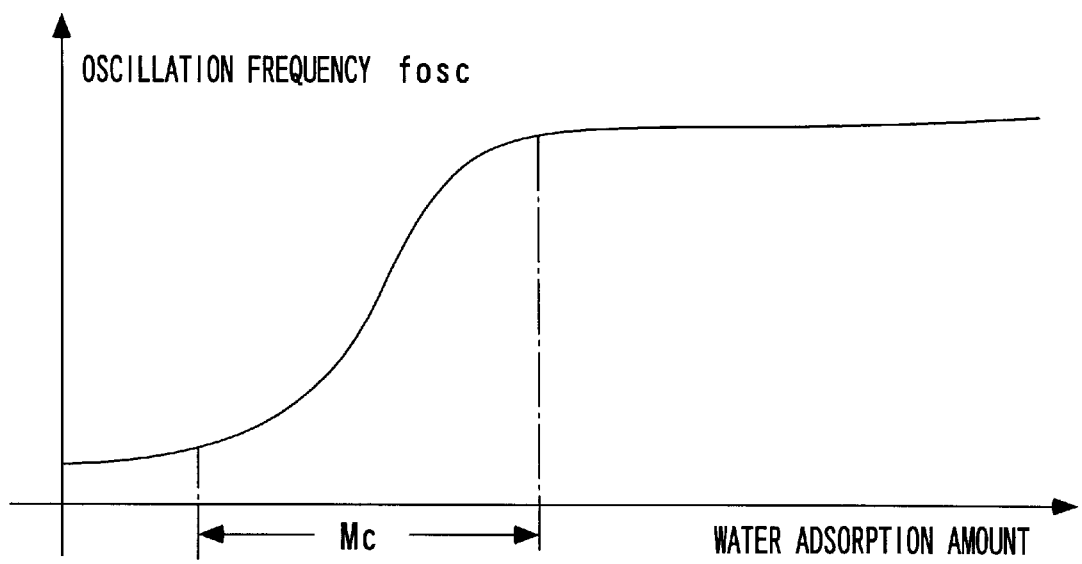
FIG. 13 is a graph which is useful in explaining a method of detecting a water adsorption amount by using, as a parameter, an oscillation frequency of a signal generated by an oscillator, and which shows the relationship between the amount of water adsorbed by the zeolite and the oscillation frequency.

(2) Method Using an Oscillation Frequency of a Signal Generated by an Oscillator as a Parameter A graph shown in FIG. 13, corresponding to the FIG. 7B graph referred to hereinabove in the first embodiment, shows that the oscillation frequency fosc of the signal generated by the oscillator 19 increases as the amount of water adsorbed by the zeolite Z on the electrodes 13 and 13 increases (see FIG. 7A for an equivalent circuit of the water adsorption amount sensor 20). As described above, changes in the oscillation frequency fosc of the signal generated by the oscillator 19 approximately agree with changes in the electrical capacitance Cs between the electrodes 13 and 13, and properly reflect the changes in the electrical capacitance Cs. Therefore, the amount of water adsorbed by the zeolite 12 of the hydrocarbon adsorber 4 can be properly detected or estimated by using the oscillation frequency fosc as a parameter.

Figure 14:
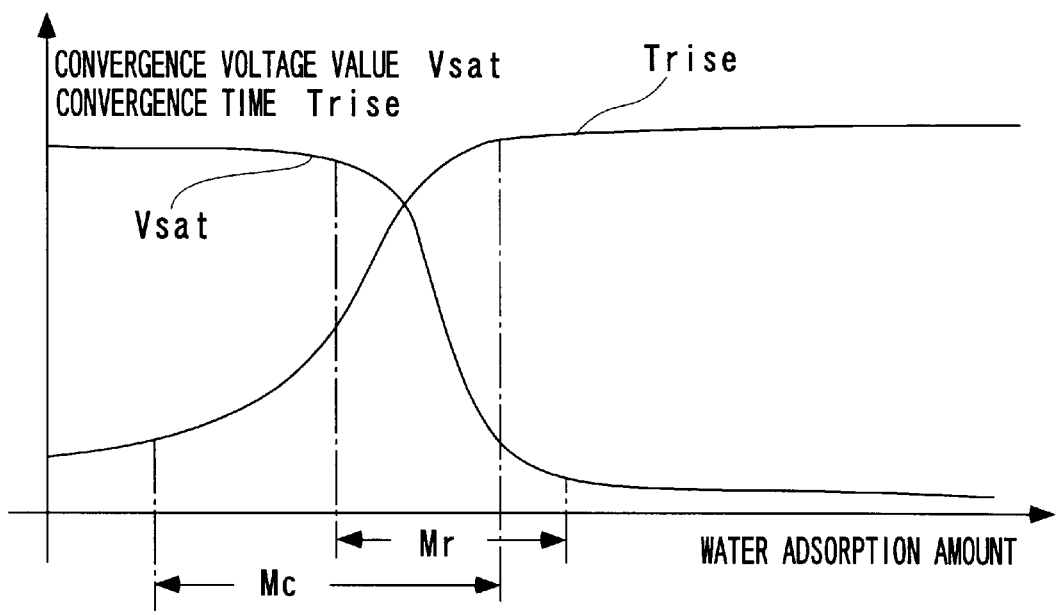
FIG. 14 is a graph useful in explaining the relationship between the amount of water adsorbed by the zeolite and the convergence voltage value/convergence time, in the case of the pulse voltage being applied between the electrodes.
Figure 15:
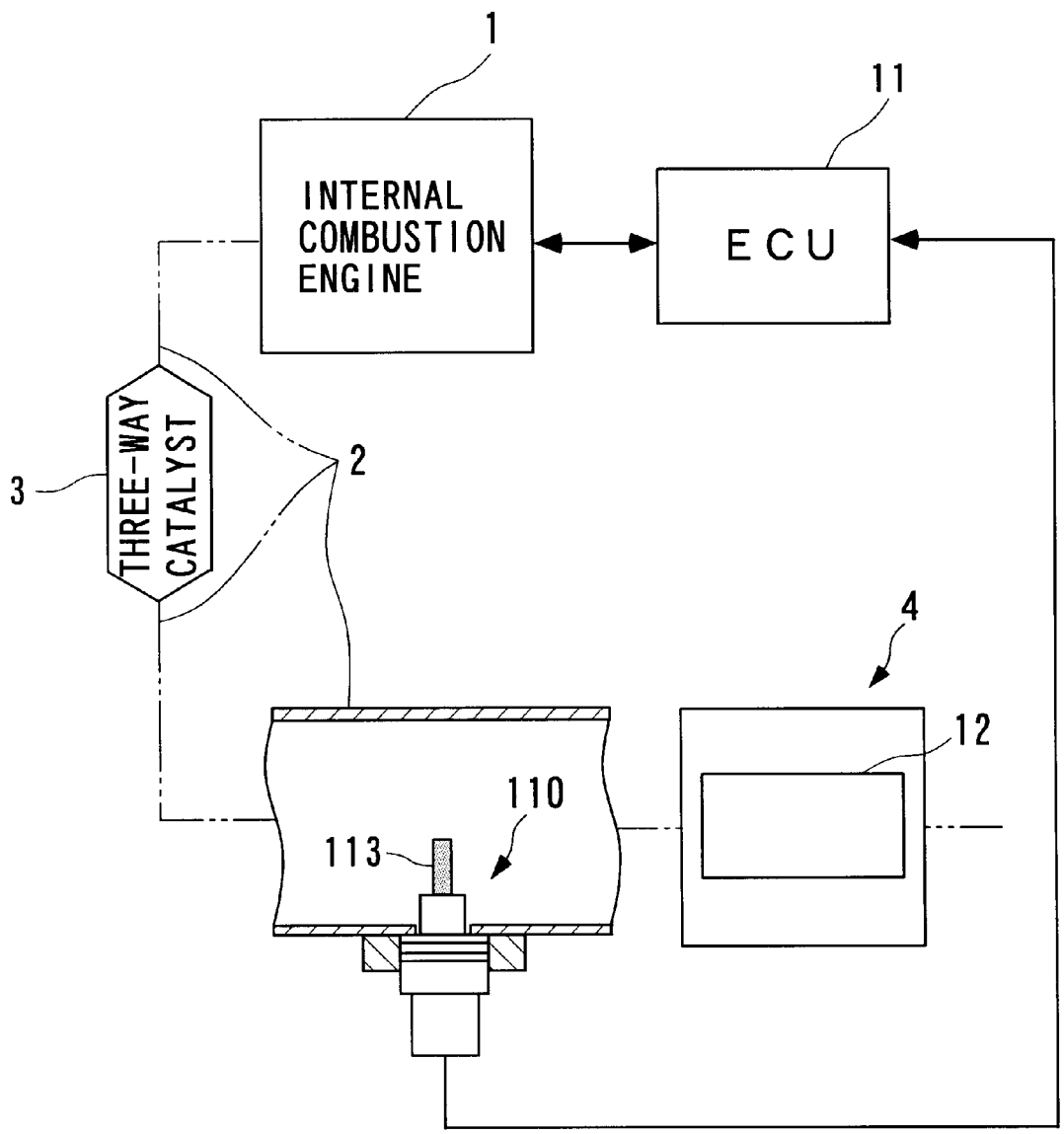
FIG. 15 is a block diagram schematically showing the arrangement of a coking sensor for an internal combustion engine, according to a third embodiment of the invention, in a state incorporated in an exhaust pipe of the engine.

(3) Method Using a Convergence Voltage Value Between the Electrodes, and a Convergence Time A graph shown in FIG. 14, corresponding to the FIG. 9 graph referred to hereinabove in the first embodiment, shows that the convergence voltage value Vsat of a voltage Vs generated between the electrodes 13 and 13 by applying a predetermined rectangular pulse voltage Vin between the electrodes 13 and 13 decreases as the amount of water adsorbed by the zeolite Z on the electrodes 13 and 13 increases. Further, the FIG. 14 graph shows that the convergence time Trise of the voltage Vs increases as the amount of water adsorbed by the zeolite Z on the electrodes 13 and 13 increases (see FIG. 8A for an equivalent circuit of the water adsorption amount sensor 20). Thus, changes in the convergence voltage value Vsat of the voltage Vs generated between the electrodes 13 and 13 by application of the predetermined pulse voltage between the electrodes 13 and 13 and the convergence time Trise approximately agree with the changes in the resistance value Rs and the electrical capacitance Cs between the electrodes 13 and 13 and properly reflect the changes in the resistance value Rs and the electrical capacitance Cs. Therefore, the amount of water adsorbed by the zeolite 12 of the hydrocarbon adsorber 4 can be properly detected or estimated by using at least one of the convergence voltage value Vsat and the convergence time Trise as a parameter.

Although in the second embodiment, the water adsorption amount sensor 20 is arranged at a location downstream of the hydrocarbon adsorber 4, this is not limitative, but it may be provided at a location upstream of the hydrocarbon adsorber 4. Further, the electrodes 13 of the water adsorption amount sensor 20 may be comprised of three or more electrodes.

Further, although in the second embodiment, the water adsorption amount sensor 20 is used as an adsorption amount sensor for detecting an amount of water adsorbed by the zeolite 12 of the hydrocarbon adsorber 4, the water adsorption amount sensor 20 is not limited to the use of detecting the amount of water adsorbed by the hydrocarbon adsorber 4, but it can be used for instance, as an adsorption amount sensor for detecting an amount of water adsorbed by a water adsorber having a zeolite for adsorbing water in exhaust gases. Further, an adsorbent used in such a water adsorber for adsorbing water is not limited to a zeolite, but any suitable adsorbent other than the zeolite may be used. In this case, it is possible to detect the amount of water adsorbed by the water adsorber, by causing an adsorbent having the same properties as those of the adsorbent of the water adsorber to be carried on the electrodes of the sensor.

Further, the water adsorption amount sensor 20 is not limited to the use of detecting an amount of water adsorbed by the above water adsorber itself, but it can also be applied, for instance, to a water amount sensor for directly detecting an amount of water in exhaust gases. Still further, the water adsorption amount sensor 20 can also be applied to a water amount sensor for directly detecting an amount of water in the atmosphere in which the sensor is disposed. When the water adsorption amount sensor 20 is used as a water amount sensor as well, it is possible to obtain the same effects as obtained by the second embodiment.

Further, the details of the construction of the hydrocarbon adsorption amount sensor in the first embodiment and those of the construction of the water adsorption amount sensor in the second embodiment are described only by way of example, and they can be varied as required so long as the same do not depart from the scope of the invention.

Next, a coking sensor for an internal combustion engine, according to a third embodiment of the invention will be described with reference to FIGS. 15 to 23. The third embodiment is distinguished from the first embodiment in that in place of the adsorption amount sensor 10, a coking sensor 110 is inserted into an exhaust pipe 2 of the engine, for detecting an amount of coke deposition on the inner surfaces of the exhaust pipe. It should be noted that in the following description, component parts and elements similar to those of the first embodiment are designated by identical reference numerals, and detailed description thereof is omitted. The coking sensor 110 and the internal combustion engine 1 are electrically connected to an ECU 11, which notifies a driver of a vehicle on which the engine 1 is installed, of results of detection carried out by the coking sensor 110, and controls the engine 1.

Figure 16A:
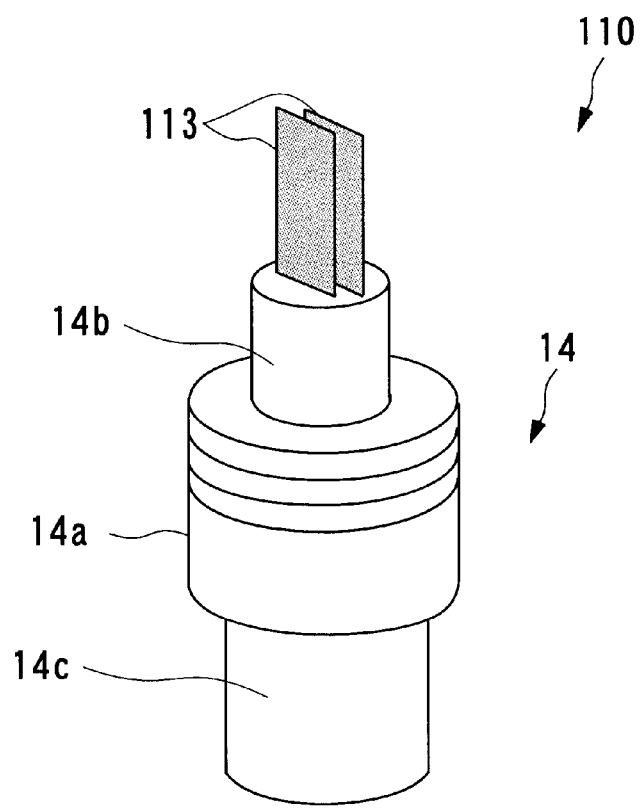
FIG. 16A is a perspective view showing an appearance of the coking sensor.
Figure 16B:
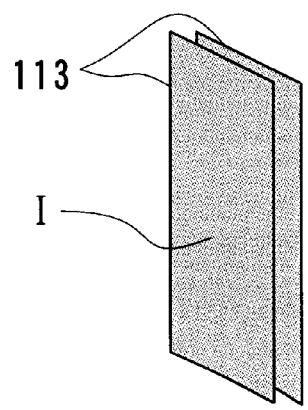
FIG. 16B is a perspective view showing an appearance of electrodes appearing in FIG. 16A.

Referring to FIGS. 16A and 16B, the coking sensor 110 includes a pair of electrodes 113 and 113 arranged such that they are opposed to each other with a predetermined gap therebetween, an electrode-supporting member 14 for supporting the electrodes 113 and 113 and a sensor circuit 15 (coke deposition amount-detecting means, see FIG. 18) contained in the electrode-supporting member 14. Each electrode 13 is formed of an electrically conductive and heat-resistant material, such as a copper alloy plate, and has a surface thereof coated with an insulating material I.

Figure 17:
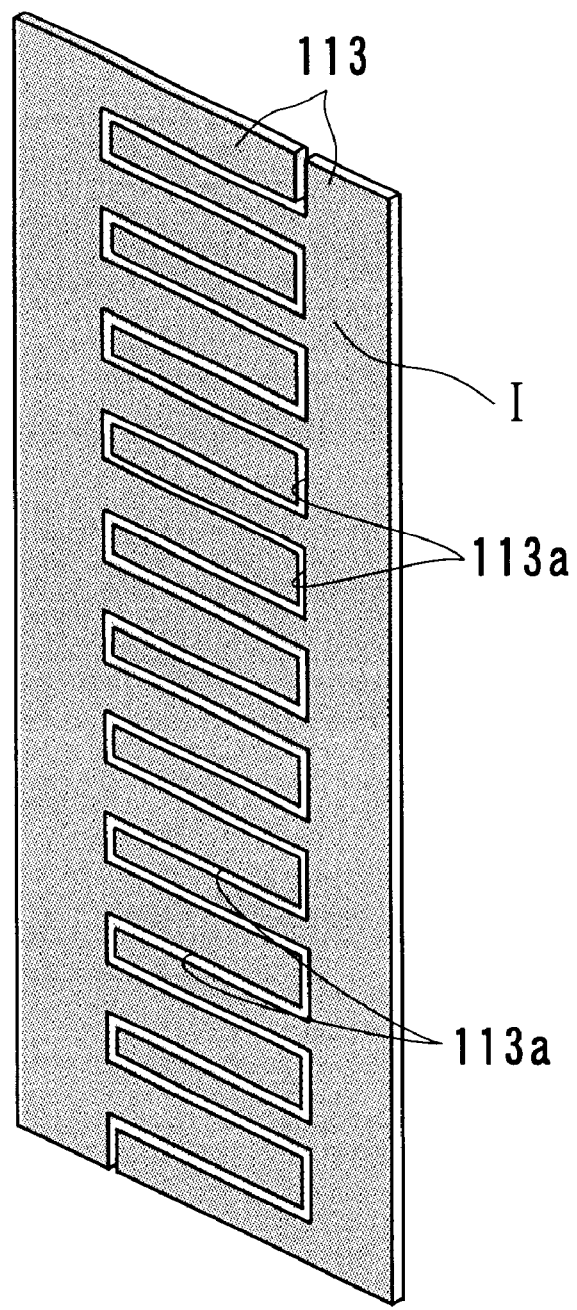
FIG. 17 is a perspective view showing an appearance of electrodes formed differently from the FIG. 16B electrodes to have a comb teeth-like shape.

As shown in FIG. 17, each of the pair of electrodes 113 and 113 may be formed to have a hair comb-like shape. In this case, opposed portions of the electrodes 113 are formed to have a shape of teeth of a hair comb, and the electrodes 113 and 113 are arranged on a substrate, not shown, formed of a heat-resistant insulating material, such that the teeth-shaped portions mate with each other and at the same time spaced from each other by a predetermined distance such that the opposed mating portions are not in contact with each other. Further, in forming the hair comb-shaped electrodes 113 and 113 arranged as above, a metal plate having a rectangular shape is rigidly fixed to the above substrate, and after forming a gap 113a shown in FIG. 17 by etching, the surface of the metal plate may be coated with the insulating material I. The hair comb-shaped electrodes 113 and 113 can be produced very easily by the method described above. The remaining details of construction of the coking sensor 110 are similar to those of construction of the adsorption amount sensor 10 of the first embodiment, and hence detailed description thereof will be omitted.

The coking sensor 110 constructed as above is attached to the exhaust pipe 2 such that the electrodes 113 and 113 and the supporting block 14b are inserted into the exhaust pipe 2.

Figure 19A:
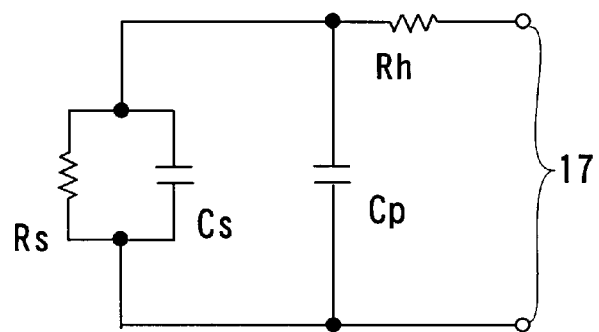
FIG. 19A is an equivalent circuit of the coking sensor.
Figure 19B:
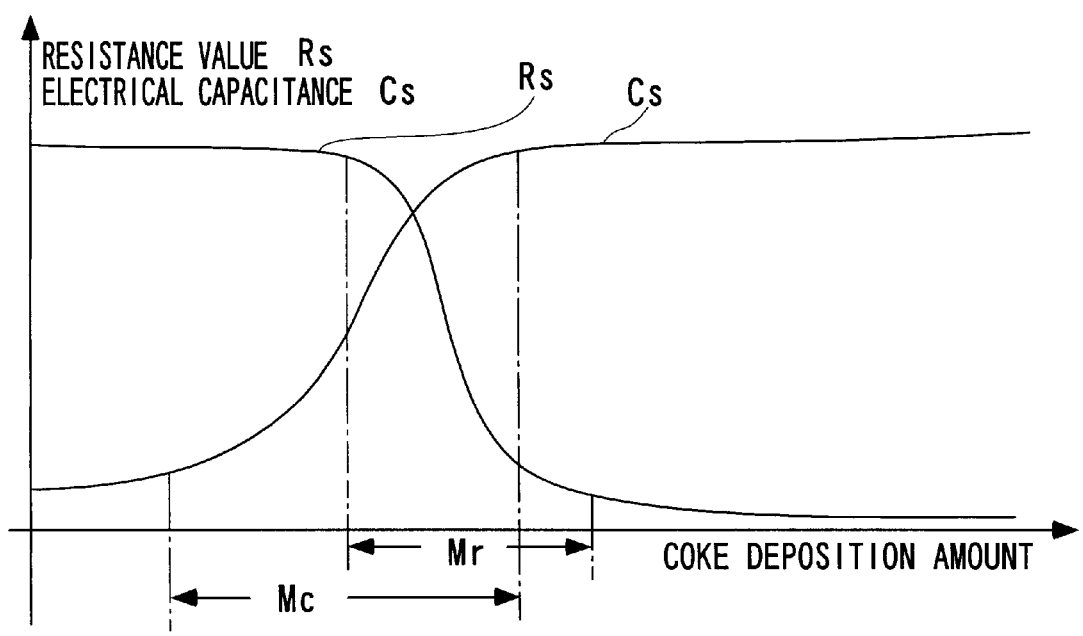
FIG. 19B is a graph useful in explaining the relationship between an amount of coke deposition within the exhaust pipe, and a resistance value between the electrodes and an electrical capacitance between the electrodes.

FIG. 19A shows an equivalent circuit of the coking sensor 110. When the predetermined voltage is applied to the input terminals 17 and 17 in the figure, the resistance value Rs and the electrical capacitance Cs between the electrodes 113 and 113 vary, as shown in FIG. 19B, with the amount of coke deposition (amount of coke deposited) on the coated surface of the electrodes 113. More specifically, the resistance value Rs progressively decreases as the amount of coke deposition increases, and it sharply decreases when the amount of coke deposition lies within a predetermined range Mr, but it again progressively decreases after the amount of coke deposition exceeds the predetermined range Mr. On the other hand, the electrical capacitance Cs progressively increases as the amount of coke deposition increases, and it sharply increases when the amount of coke deposition lies within a predetermined range Mc, but it again progressively increases after the amount of coke deposition exceeds the predetermined range Mc.

It should be noted that the coking sensor 110 is configured such that the resistance value Rs and the electrical capacitance Cs between the electrodes 113 and 113 are far larger than a resistance value Rh of a harness in the sensor circuit 15 and a parasitic capacitance Cp by the harness. Accordingly, the resistance value Rs and the electrical capacitance Cs between the electrodes 113 and 113 vary with the amount of coke deposition on the electrodes 113 and 113, without being affected by the resistance value Rh and the parasitic capacitance Cp.

According to the coking sensor 110 configured as above, the electrodes 113 and 113 coated with the insulating material I are arranged within the exhaust pipe 2 in a manner opposed to each other, and coke or soot deposits on the insulating material-coated surface of the electrodes 113 and 113, so that the resistance value Rs and the electrical capacitance Cs between the electrodes 113 and 113 vary with the amount of coke deposition. This makes it possible to detect the amount of coke deposition within the exhaust pipe 2, by using the parameter indicative of changes in at least one of the resistance value Rs and the electrical capacitance Cs between the electrodes 113 and 113. In other words, since coke or soot tends to deposit on the inner wall of the exhaust pipe 2 and the electrodes 113 and 113 substantially in the same manner, by detecting the amount of coke deposition on the coated surface of the electrodes 113 and 113 by the sensor circuit 15 by using this parameter, the amount of coke deposition within the exhaust pipe 2 can be accurately detected. When the coking sensor 110 is arranged, as in this embodiment, at a location close to the hydrocarbon adsorber 4, the degradation of the zeolite 12 of the hydrocarbon adsorber 4 can be indirectly determined.

Further, differently from the conventional method of directly measuring a weight of the exhaust pipe 2, it is possible to easily detect an amount of coke deposition (coke deposition amount) and during operation of the internal combustion engine 1, without removing the exhaust pipe 2 from the engine 1. Further, since the surface of each electrode 113 is coated with the insulating material I, it is possible to positively prevent the electrodes from being short-circuited by coke or soot depositing between the electrodes 113.

As shown in FIG. 19B, the predetermined ranges Mr and Mc of the coke deposition amount, within which the resistance value Rs and the electrical capacitance Cs between the electrodes 113 and 113 sharply change with the coke deposition amount, are not coincident with each other but partially overlapping each other. Therefore, the coke deposition amount can be detected by using both the resistance value Rs and the electrical capacitance Cs between the electrodes 113 and 113, whereby it is possible to detect a wider range of the coke deposition amount with higher accuracy than when the coke deposition amount is detected by using only one of the resistance value Rs and the electrical capacitance Cs.

Next, methods of detecting the coke deposition amount by using several kinds of parameters based on the resistance value Rs and the electrical capacitance Cs between the electrodes 113 and 113 will be described with reference to FIGS. 20A to 23. In the following, (1) a method using a voltage between electrodes as a parameter, (2) a method using an oscillation frequency of a signal generated by an oscillator as a parameter, and (3) a method using a convergence voltage value to which converges a voltage between electrodes and a convergence time, as parameters, will be described one by one.

(1) Method Using a Voltage Between Electrodes as a Parameter

Figure 20A:
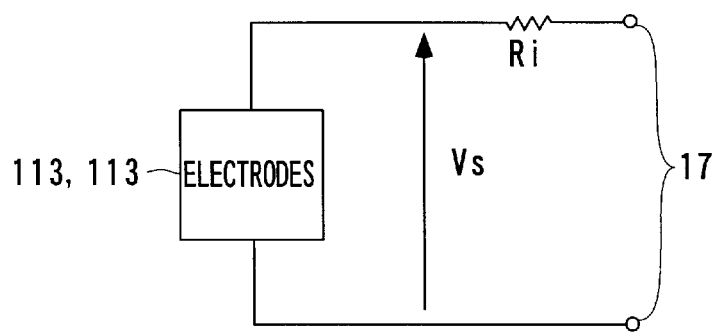
Figure 20B:
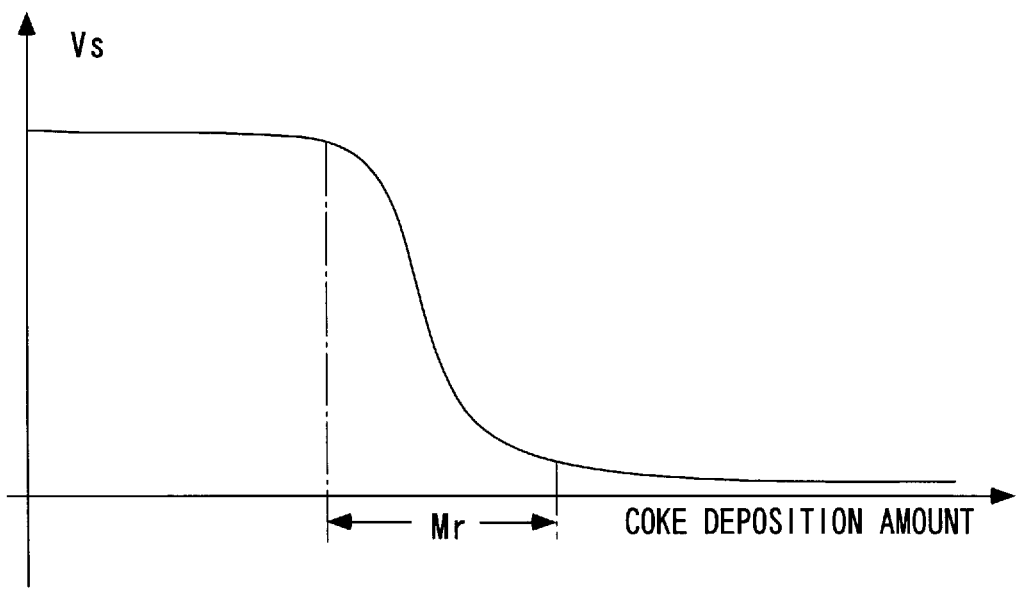

FIG. 20A schematically shows an equivalent circuit of the coking sensor 110 employing the method using a voltage generated between the electrodes 113 and 113 by applying a predetermined DC voltage therebetween. In this case, the electrodes 113 and 113 function as a resistance. Ri in the figure designates a resistance arranged in the sensor circuit 15, which is connected in series with the electrodes 113 and 113. In the circuit constructed as above, when the predetermined DC voltage is applied between the electrodes 113 and 113 via the input terminals 17 and 17, the voltage Vs generated between the electrodes 113 and 113 decreases as the amount of coke deposition on the electrodes 113 and 113 increases. More specifically, as shown in FIG. 6B, the voltage Vs progressively decreases as the amount of coke deposition on the electrodes 113 and 113 increases, and it sharply decreases when the amount of coke deposition lies within the predetermined range Mr. The voltage Vs again progressively decreases after the amount of coke deposition exceeds the predetermined range Mr.

In other words, changes in the voltage Vs generated between the electrodes 113 and 113 by application of the above predetermined DC voltage between the electrodes 113 and 113 approximately agree with changes in the resistance value Rs between the electrodes 113 and 113 and properly reflect the changes in the resistance value Rs. Therefore, the amount of coke deposition within the exhaust pipe 2 can be properly detected by using, as a parameter, the voltage Vs generated between the electrodes 113 and 113 through the application of the predetermined DC voltage.

Figure 21A:
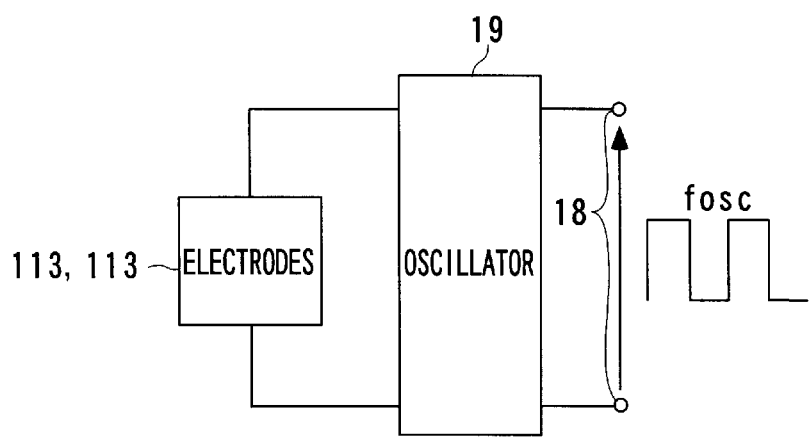
Figure 21B:
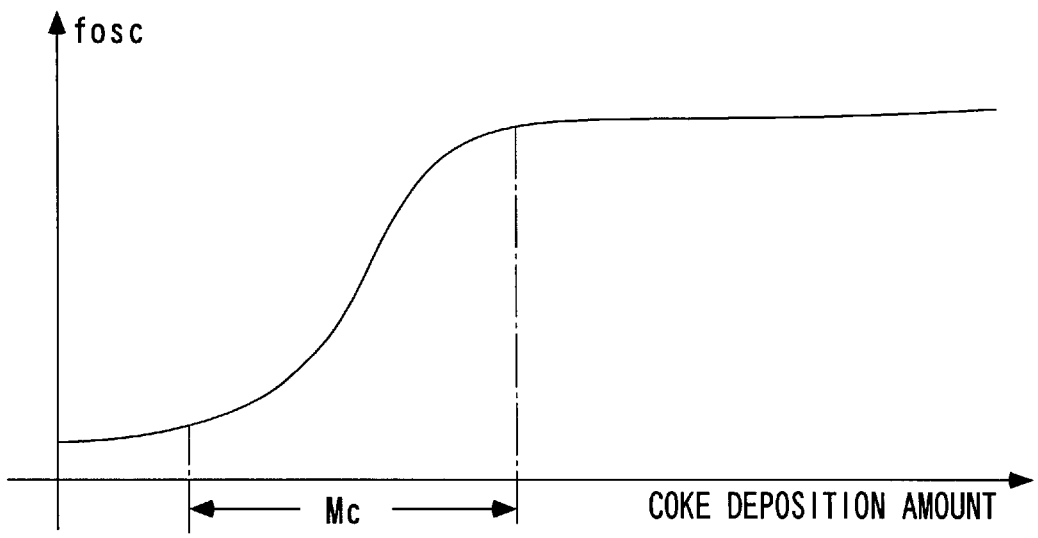

(2) Method Using an Oscillation Frequency of a Signal Generated by an Oscillator as a Parameter FIG. 21A schematically shows an equivalent circuit of the coking sensor 110, in which the oscillator 19 is incorporated in the sensor circuit 15. The oscillator 19 is configured such that a signal having an oscillation frequency fosc dependent on the electrical capacitance Cs between the electrodes 113 and 113 is output from the output terminals 18 and 18. In the circuit constructed as above, the oscillation frequency fosc of the signal generated by the oscillator 19 increases as the amount of coke deposition on the electrodes 113 and 113 increases. More specifically, as shown in FIG. 21B, the oscillation frequency fosc progressively increases as the amount of coke deposition on the electrodes 113 and 113 increases, and it sharply increases when the amount of coke deposition lies within the predetermined range Mc. The oscillation frequency fosc again progressively increases after the amount of coke deposition exceeds the predetermined range Mc.

In other words, changes in the oscillation frequency fosc of the signal generated by the oscillator 19 approximately agree with changes in the electrical capacitance Cs between the electrodes 113 and 113 and properly reflect the changes in the electrical capacitance Cs. Therefore, the amount of coke deposition within the exhaust pipe 2 can be properly detected by using the oscillation frequency fosc as a parameter.

Figure 23:
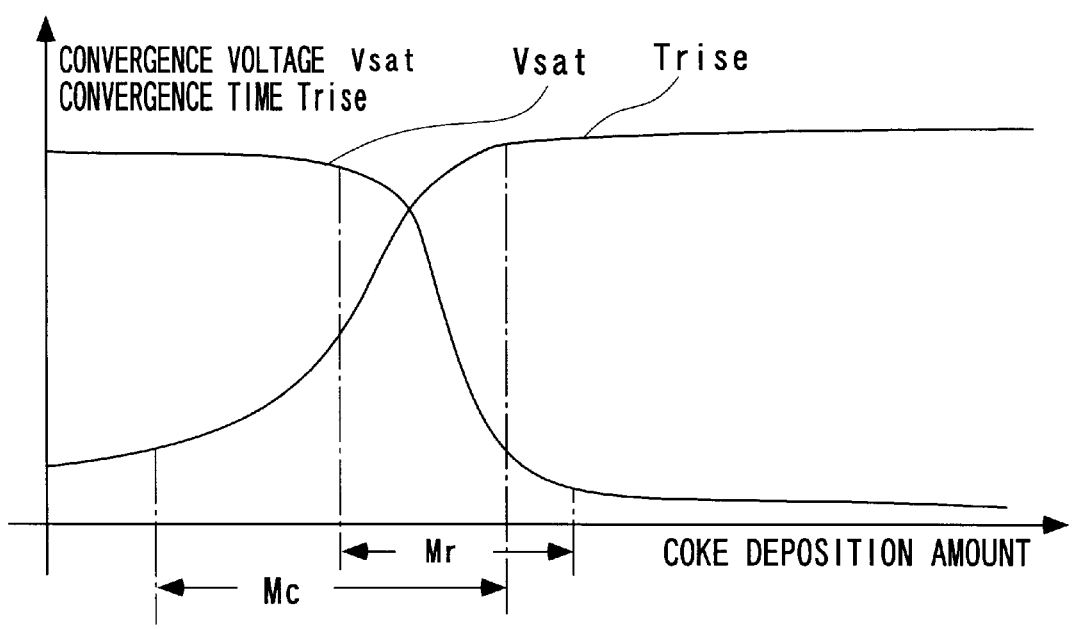
FIG. 23 is a graph useful in explaining the relationship between the amount of coke deposition within the exhaust time, and the convergence voltage/convergence time, in the case of the pulse voltage being applied between the electrodes.

The above oscillator 19 is not limited to one which outputs the signal having an oscillation frequency dependent on the electrical capacitance Cs between the electrodes 113 and 113, but the oscillator 19 may be configured such that it outputs a signal having an oscillation frequency dependent on the resistance value Rs between the electrodes 113 and 113, in place of or in combination with the signal having the oscillation frequency dependent on the electrical capacitance Cs. In this case, changes in the oscillation frequency approximately agree with changes in the resistance value Rs between the electrodes 113 and 113 and properly reflect the changes in the resistance value Rs. Therefore, the amount of coke deposition within the exhaust pipe 2 can be further properly detected. Further, the oscillator may be provided outside the sensor circuit 15, e.g. within the ECU (3) Method Using a Convergence Voltage Value Between the Electrodes, and a Convergence Time as Parameters FIG. 22A schematically shows an equivalent circuit of the coking sensor 110 employing the method using the convergence voltage value and the convergence time measured by applying a predetermined rectangular pulse voltage Vin between the electrodes 113 and 113. In the circuit constructed as shown in FIG. 22A, when the predetermined pulse voltage Vin is applied between the electrodes 113 and 113 via the input terminals 17 and 17, a voltage Vs generated between the electrodes 113 and 113 converges to a convergence voltage value Vsat dependent on the amount of coke deposition on the electrodes 113 and 113. The convergence voltage value Vsat of the voltage Vs decreases as the amount of coke deposition on the electrodes 113 and 113 increases. More specifically, as shown in FIG. 23, the convergence voltage value Vsat progressively decreases as the amount of coke deposition on the electrodes 113 and 113 increases, and it sharply decreases when the amount of coke deposition lies within the predetermined range Mr. The convergence voltage value Vsat again progressively decreases after the amount of coke deposition exceeds the predetermined range Mr. On the other hand, the convergence time Trise increases as the amount of coke deposition on the electrodes 113 and 113 increases. More specifically, as shown in FIG. 23, the convergence time Trise progressively increases as the amount of coke deposition on the electrodes 113 and 113 increases, and it sharply increases when the amount of coke deposition lies within the predetermined range Mc. The convergence time Trise again progressively increases after the amount of coke deposition exceeds the predetermined range Mc.

In other words, changes in the convergence voltage value Vsat to which converges the voltage Vs generated between the electrodes 113 and 113 upon application of the above predetermined pulse voltage between the electrodes 113 and 113 and the convergence time Trise approximately agree with the changes in the resistance value Rs and the electrical capacitance Cs between the electrodes 113 and 113 and properly reflect the resistance value Rs and the electrical capacitance Cs. Therefore, the amount of coke deposition within the exhaust pipe 2 can be properly detected by using at least one of the convergence voltage value Vsat and the convergence time Trise as a parameter.

The third embodiment is not limited to the illustrated examples described in detail hereinabove, but various variations and modifications thereof are possible. For instance, the electrodes 113 of the coking sensor 110 may be comprised of three or more electrodes. In this case, the amount of coke deposition on the coated surface of the electrodes 113 can be detected more accurately, thereby making it possible to detect the amount of coke deposition within the exhaust pipe 2 with higher accuracy. Further, although in the third embodiment described above, the coking sensor is inserted into the exhaust pipe, this is not limitative but the same may be inserted into the EGR pipe which can have coke or soot deposit on its inner wall, and in this case as well, the amount of coke deposition on the inner wall of the EGR pipe can be accurately detected.

It is further understood by those skilled in the art that the foregoing are preferred embodiments of the invention, and that various changes and modifications may be made without departing from the spirit and scope thereof.

What is claimed is:

1. An adsorption amount sensor for detecting an amount of hydrocarbons adsorbed by a zeolite of a hydrocarbon adsorber, for purifying exhaust gases, that adsorbs hydrocarbons in the exhaust gases by using said zeolite, the adsorption amount sensor comprising:

a plurality of electrodes carrying zeolite thereon with said electrodes spaced apart from each other by a predetermined gap and arranged in the vicinity of said hydrocarbon adsorber there being no zeolite in the gap between said electrodes; and a hydrocarbon adsorption amount-detecting means for detecting said amount of hydrocarbons adsorbed by said zeolite, by using a parameter indicative of changes in at least one of a resistance value between said electrodes and an electrical capacitance between said electrodes.

2. An adsorption amount sensor according to claim 1, wherein said parameter is a voltage generated between said electrodes by application of a predetermined DC voltage between said electrodes.

3. An adsorption amount sensor according to claim 1, further including an oscillator for outputting a signal having an oscillation frequency dependent on said at least one of said resistance value between said electrodes and said electrical capacitance between said electrodes, and wherein said parameter is said oscillation frequency of said signal.

4. An adsorption amount sensor according to claim 1, wherein said parameter is at least one of a convergence voltage value to which converges a voltage generated between said electrodes by application of a pulse voltage between said electrodes, and a convergence time.

5. An adsorption amount sensor according to claim 1, wherein said electrodes have respective portions opposed to each other, said respective portions each having a shape of teeth of a hair comb, and mating with each other in a manner spaced from each other.

6. An adsorption amount sensor according to claim 1, wherein said hydrocarbon adsorber is arranged within an exhaust pipe of an internal combustion engine, and wherein said adsorption amount sensor detects said amount of hydrocarbons adsorbed from said exhaust gases from said internal combustion engine by said hydrocarbon adsorber, by using said parameter.

7. An adsorption amount sensor according to claim 6, wherein said adsorption amount sensor is arranged in said exhaust pipe at a location upstream of said hydrocarbon adsorber.

8. An adsorption amount sensor for detecting an amount of water adsorbed by a zeolite of a hydrocarbon adsorber, for purifying exhaust gases, that adsorbs hydrocarbons and water in the exhaust gases by using said zeolite, the adsorption amount sensor comprising:

a plurality of electrodes carrying zeolite thereon with said electrodes spaced apart from each other by a Predetermined gap and arranged in the vicinity of said hydrocarbon adsorber, there being no zeolite in the gap between said electrodes; and a water adsorption amount-detecting means for detecting said amount of water adsorbed by said zeolite, by using a parameter indicative of changes in at least one of a resistance value between said electrodes and an electrical capacitance between said electrodes.

9. An adsorption amount sensor according to claim 8, wherein said parameter is a voltage generated between said electrodes by application of a predetermined DC voltage between said electrodes.

10. An adsorption amount sensor according to claim 8, further including an oscillator for outputting a signal having an oscillation frequency dependent on said at least one of said resistance value between said electrodes and said electrical capacitance between said electrodes, and wherein said parameter is said oscillation frequency of said signal.

11. An adsorption amount sensor according to claim 8, wherein said parameter is at least one of a convergence voltage value to which converges a voltage generated between said electrodes by application of a pulse voltage between said electrodes, and a convergence time.

12. An adsorption amount sensor according to claim 8, wherein said electrodes have respective portions opposed to each other, said respective portions each having a shape of teeth of a hair comb, and mating with each other in a manner spaced from each other.

13. An adsorption amount sensor according to claim 8, wherein said hydrocarbon adsorber is arranged within an exhaust pipe of an internal combustion engine, and wherein said adsorption amount sensor detects said amount of water adsorbed from said exhaust gases from said internal combustion engine by said hydrocarbon adsorber, by using said parameter.

14. An adsorption amount sensor according to claim 13, wherein said adsorption amount sensor is arranged in said exhaust pipe at a location downstream of said hydrocarbon adsorber.

15. A coking sensor for an internal combustion engine having a pipe, the coking sensor detecting an amount of coke deposition on inner surfaces of said pipe, the coking sensor comprising:

a plurality of electrodes arranged within said pipe in a manner opposed to each other and each having a surface thereof coated with an insulating material; and coke deposition amount-detecting means for detecting said amount of coke deposition, by using a parameter indicative of changes in at least one of a resistance value between said electrodes and an electrical capacitance between said electrodes.

16. A coking sensor according to claim 15, wherein said parameter is a voltage generated between said electrodes by application of a predetermined DC voltage between said electrodes.

17. A coking sensor according to claim 15, further including an oscillator for outputting a signal having an oscillation frequency dependent on said at least one of said resistance value between said electrodes and said electrical capacitance between said electrodes, and wherein said parameter is said oscillation frequency of said signal.

18. A coking sensor according to claim 15, wherein said parameter is at least one of a convergence voltage value to which converges a voltage generated between said electrodes by application of a pulse voltage between said electrodes, and a convergence time.

19. A coking sensor according to claim 15, wherein said electrodes have respective portions opposed to each other, said respective portions each having a shape of teeth of a hair comb, and mating with each other in a manner spaced from each other.

* * * * *